(12) United States Patent
Yamamoto et al.

(10) Patent No.: US 9,604,905 B2
(45) Date of Patent: Mar. 28, 2017

(54) ISOMERIZATION METHOD FOR BIS (AMINOMETHYL) CYCLOHEXANE

(71) Applicant: MITSUBISHI GAS CHEMICAL COMPANY, INC., Chiyoda-ku (JP)

(72) Inventors: Yoshiaki Yamamoto, Niigata (JP); Yuko Sameshima, Niigata (JP); Takuya Okamura, Niigata (JP)

(73) Assignee: MITSUBISHI GAS CHEMICAL COMPANY, INC., Chiyoda-ku (JP)

(*) Notice: Subject to any disclaimer, the term of this patent is extended or adjusted under 35 U.S.C. 154(b) by 0 days.

(21) Appl. No.: 14/916,882

(22) PCT Filed: Sep. 17, 2014

(86) PCT No.: PCT/JP2014/074597
§ 371 (c)(1),
(2) Date: Mar. 4, 2016

(87) PCT Pub. No.: WO2015/041262
PCT Pub. Date: Mar. 26, 2015

(65) Prior Publication Data
US 2016/0207877 A1    Jul. 21, 2016

(30) Foreign Application Priority Data

Sep. 17, 2013 (JP) .................. 2013-191882
Mar. 19, 2014 (JP) .................. 2014-056149
May 29, 2014 (JP) .................. 2014-110871

(51) Int. Cl.
| C07C 209/68 | (2006.01) |
| C07C 211/18 | (2006.01) |
| C07C 249/02 | (2006.01) |
| C07C 251/24 | (2006.01) |
| C07C 209/86 | (2006.01) |

(52) U.S. Cl.
CPC .......... *C07C 209/68* (2013.01); *C07C 209/86* (2013.01); *C07C 211/18* (2013.01); *C07C 249/02* (2013.01); *C07C 251/24* (2013.01); *C07C 2101/14* (2013.01)

(58) Field of Classification Search
None
See application file for complete search history.

(56) References Cited

U.S. PATENT DOCUMENTS

| 3,344,164 A | 9/1967 | Seaton |
| 3,829,490 A | 8/1974 | Mueller et al. |
| 4,020,104 A | 4/1977 | Richter et al. |
| 4,058,563 A | 11/1977 | Richter |
| 4,086,276 A | 4/1978 | Butte, Jr. |
| 5,969,187 A | 10/1999 | Okawa et al. |
| 2012/0116122 A1 | 5/2012 | Feist et al. |
| 2013/0324631 A1 | 12/2013 | Kuwamura et al. |

FOREIGN PATENT DOCUMENTS

| JP | 48-29741 A | 4/1973 |
| JP | 50-126638 A | 10/1975 |
| JP | 53-37649 A | 4/1978 |
| JP | 53-130637 A | 11/1978 |
| JP | 54-41804 A | 4/1979 |
| JP | 62-3144 B2 | 1/1987 |
| JP | 10-259167 A | 9/1998 |
| JP | 10-306066 A | 11/1998 |
| JP | 10-330329 A | 12/1998 |
| JP | 11-335335 A | 12/1999 |
| JP | 2001-131115 A | 5/2001 |
| JP | 2013-500994 A | 1/2013 |
| WO | WO 2009/051114 A1 | 4/2009 |

OTHER PUBLICATIONS

International Search Report issued Oct. 28, 2014, in PCT/JP2014/074597 filed Sep. 17, 2014.
K. Ronbunshu, Japanese Journal of Polymer Science and Technology, vol. 36, No. 5, pp. 305-310, (1979).
F.R. Prince et al., "Cis/Trans Copolyamides of 1,4-Bisaminomethylcyclohexane", Journal of Polymer Science: Part A-1, vol. 10, pp. 465-470, (1972).

*Primary Examiner* — Sudhakar Katakam
*Assistant Examiner* — Jennifer C Sawyer
(74) *Attorney, Agent, or Firm* — Oblon, McClelland, Maier & Neustadt, L.L.P.

(57) ABSTRACT

A method for isomerizing a bis(aminomethyl)cyclohexane, including an isomerization step of isomerizing the bis(aminomethyl)cyclohexane in the presence of an imine compound represented by the following general formula (1) and at least one compound selected from the group consisting of an alkali metal, an alkali metal-containing compound, an alkaline earth metal and an alkaline earth metal-containing compound:

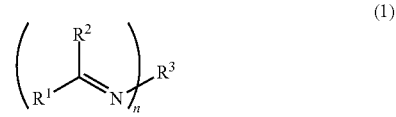

(1)

wherein $R^1$ and $R^2$ each independently represent a hydrogen atom or a monovalent group selected from the group consisting of a substituted or unsubstituted hydrocarbon group, a substituted or unsubstituted alkoxy group, and an acyl group ($R^1$ and $R^2$ may mutually bind to form a ring); $R^3$ represents a hydrogen atom or an n-valent group selected from the group consisting of substituted or unsubstituted hydrocarbon groups; and n represents an integer of 1 to 10.

20 Claims, 21 Drawing Sheets

ISOMERIZATION METHOD FOR BIS(AMINOMETHYL) CYCLOHEXANE

TECHNICAL FIELD

The present invention relates to an isomerization method for bis(aminomethyl)cyclohexane.

BACKGROUND ART

Bis(aminomethyl)cyclohexane is an industrially important compound to be used as a raw material for e.g., epoxy hardeners, polyamides and polyurethanes. A bis(aminomethyl)cyclohexane has two isomers, i.e., a cis-isomer and a trans-isomer, derived from the cyclohexane ring. It is known that the physical properties of a polymer obtained by using a bis(aminomethyl)cyclohexane greatly vary depending upon the ratio of isomers, i.e., ratio of a cis-isomer and a trans-isomer.

For example, in a polyamide obtained by using 1,4-bis(aminomethyl)cyclohexane, it is known that, as the content of a trans-isomer increases, the melting point of the polyamide increases, with the result that the polyamide becomes highly heat resistant (Non Patent Literature 1). It is also known that a polyurethane obtained by using 1,4-bisisocyanatomethyl cyclohexane derived from 1,4-bis(aminomethyl)cyclohexane is improved in physical properties required for various applications as the content of the trans-isomer increases (Patent Literature 1).

It is further shown that, in a polyamide obtained by using 1,3-bis(aminomethyl)cyclohexane, a polyamide having a high cis-isomer content has a high crystallinity; whereas a polyamide having a high trans-isomer content is amorphous (Non Patent Literature 2).

For these reasons, it is extremely important to control the isomer ratio of a bis(aminomethyl)cyclohexane.

CITATION LIST

Patent Literatures

Patent Literature 1: International Publication No. WO2009/051114
Patent Literature 2: Japanese Patent Laid-Open No. S54-41804
Patent Literature 3: Japanese Patent Laid-Open No. S50-126638
Patent Literature 4: Japanese Patent Laid-Open No. H10-259167
Patent Literature 5: Japanese Patent Laid-Open No. H10-306066
Patent Literature 6: Japanese Patent Laid-Open No. H11-335335
Patent Literature 7: Japanese Patent Publication No. S62-3144
Patent Literature 8: Japanese Patent Laid-Open No. H10-330329

Non Patent Literatures

Non Patent Literature 1: J. Polym. Sci. Part A-1, 10, 465 (1972)
Non Patent Literature 2: KOBUNSHI RONBUNSHU (Japanese Journal of Polymer Science and Technology), Vol. 65, No. 5, pp. 305-310 (1979)

SUMMARY OF INVENTION

Technical Problem

A bis(aminomethyl)cyclohexane is produced by a technique known in the art. To describe more specifically, a bis(aminomethyl)cyclohexane can be obtained as follows. First, an aromatic dinitrile is hydrogenated in the presence of a catalyst to synthesize xylylenediamine. The xylylenediamine obtained is nuclear-hydrogenated in the presence of a catalyst to obtain the bis(aminomethyl)cyclohexane.

For producing xylylenediamine by hydrogenating an aromatic dinitrile, many methods are reported. For example, a method of using a Raney catalyst such as a Raney nickel and a Raney cobalt, is known (Patent Literature 2).

For producing a bis(aminomethyl)cyclohexane by nuclear-hydrogenating xylylenediamine, many methods are reported. For example, a method of using a catalyst such as ruthenium immobilized on a carrier is known (Patent Literature 3).

In the nuclear hydrogenation reaction of xylylenediamine, a cis-isomer is more easily produced than a trans-isomer, which means that it is difficult to selectively synthesize a trans-isomer. The ratio of a trans-isomer of bis(aminomethyl)cyclohexane produced by this method is generally 50% or less.

A substituent of a compound having a cyclohexane ring can take an equatorial conformation and an axial conformation; however, the equatorial conformation is generally stable. Therefore, for example, a trans conformation is stable in 1,4-bis(aminomethyl)cyclohexane and a cis configuration is stable in 1,3-bis(aminomethyl)cyclohexane. As a result, a trans-isomer is preferentially produced in isomerization of 1,4-bis(aminomethyl)cyclohexane; whereas, a cis-isomer is preferentially produced in isomerization of 1,3-bis(aminomethyl)cyclohexane.

As an isomerization method for 1,4-bis(aminomethyl)cyclohexane produced as described above, a method of obtaining trans-1,4-bis(aminomethyl)cyclohexane by isomerizing 1,4-bis(aminomethyl)cyclohexane in the presence of a noble metal catalyst such as platinum and ruthenium is known (Patent Literatures 4 to 6). In this method, the isomerization reaction must be carried out in liquid ammonia in order to improve the yield. This method has a drawback of a high-pressure reaction. Further, if liquid ammonia is not used, a high yield cannot be attained.

Another method for isomerizing 1,4-bis(aminomethyl)cyclohexane is known in which 1,4-bis(aminomethyl)cyclohexane is mixed with a benzylamine compound and an alkali metal, an alkali metal hydride or an alkali metal amide to isomerize it (Patent Literature 7). In this method, a large amount of a catalyst must be added to allow the isomerization reaction to proceed. Besides this, a benzylamine compound such as 4-methylbenzylamine used herein is industrially not easily obtained.

In another method (Patent Literature 8) known in the art, trans-1,4-bis(aminomethyl)cyclohexane is obtained by mixing 1,4-bis(aminomethyl)cyclohexane and 4-methylbenzaldehyde (2 mole equivalent) to obtain a bisaldimine compound as a derivative of 1,4-bis(aminomethyl)cyclohexane, isomerizing the bisaldimine compound, and decomposing the isomerized bisaldimine compound. In this method, a trans-isomer is obtained in an extremely high ratio of 99%; however, three steps are required for isomerization; an aldehyde for obtaining a derivative must be recycled through very complicated step. For these reasons, it is not easy to carry out this method industrially.

The present invention was carried out consideration of the aforementioned problems. An object of the present invention is to provide a method for isomerizing a bis(aminomethyl)cyclohexane, which simply and highly actively realizes an isomerization reaction of an industrially important compound, i.e., bis(aminomethyl)cyclohexane, without passing through a high-pressure reaction and a complicated multistage process.

Solution to Problem

The present inventors intensively conducted studies with a view to solving the aforementioned problems. As a result, they found that the above problems can be solved by an isomerization method having a predetermined isomerization step and arrived at the present invention.

More specifically, the present invention is as follows.

[1]

A method for isomerizing a bis(aminomethyl)cyclohexane, including an isomerization step of isomerizing a bis(aminomethyl)cyclohexane in the presence of:

an imine compound represented by the following general formula (1) and an alkali metal, an alkali metal-containing compound, an alkaline earth metal or an alkaline earth metal-containing compound.

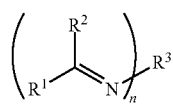
(1)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring); $R^3$ represents a hydrogen atom or an n-valent group selected from the group consisting of substituted or unsubstituted hydrocarbon groups; and n represents an integer of 1 to 10.

[2]

The method for isomerizing the bis(aminomethyl)cyclohexane according to [1], wherein the substituted or unsubstituted hydrocarbon group represented by each of $R^1$ and $R^2$ comprises a monovalent group selected from the group consisting of a substituted or unsubstituted aliphatic hydrocarbon group, a substituted or unsubstituted alicyclic hydrocarbon group and a substituted or unsubstituted aromatic hydrocarbon group; and the substituted or unsubstituted hydrocarbon group represented by $R^3$ comprises an n-valent group selected from the group consisting of a substituted or unsubstituted aliphatic hydrocarbon group, a substituted or unsubstituted alicyclic hydrocarbon group and a substituted or unsubstituted aromatic hydrocarbon group.

[3]

The method for isomerizing the bis(aminomethyl)cyclohexane according to [1] or [2], wherein the imine compound comprises a compound represented by the following general formula (2) and/or a compound represented by the following general formula (3):

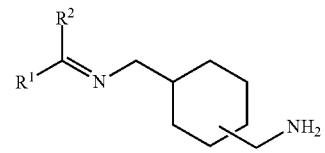
(2)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring);

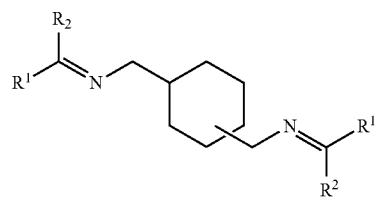
(3)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring).

[4]

The method for isomerizing the bis(aminomethyl)cyclohexane according to [2] or [3], wherein the aliphatic hydrocarbon group comprises a linear or branched and substituted or unsubstituted aliphatic hydrocarbon group.

[5]

The method for isomerizing the bis(aminomethyl)cyclohexane according to any one of [2] to [4], wherein the alicyclic hydrocarbon group comprises an alicyclic hydrocarbon group having an amino group.

[6]

The method for isomerizing the bis(aminomethyl)cyclohexane according to any one of [2] to [5], wherein the aromatic hydrocarbon group comprises a monovalent group selected from the group consisting of a substituted or unsubstituted benzyl group, a substituted or unsubstituted benzal group, a substituted or unsubstituted monovalent phenyl group and a substituted or unsubstituted monovalent naphthyl group.

[7]

The method for isomerizing the bis(aminomethyl)cyclohexane according to any one of [1] to [6], wherein the imine compound is obtained by dehydration condensation between a primary amine and an aldehyde and/or a ketone.

[8]

The method for isomerizing the bis(aminomethyl)cyclohexane according to any one of [1] to [7], wherein the imine compound is obtained by dehydration condensation between the bis(aminomethyl)cyclohexane and an aldehyde and/or a ketone.

[9]

The method for isomerizing the bis(aminomethyl)cyclohexane according to [7] or [8], wherein the aldehyde comprises at least one selected from the group consisting of an aliphatic aldehyde represented by the following general formula (6), an aromatic aldehyde represented by the following general formula (7) and an aromatic aldehyde represented by the following general formula (8):

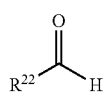
(6)

wherein $R^{22}$ represents a hydrogen atom or a monovalent substituent selected from the group consisting of a substituted or unsubstituted aliphatic hydrocarbon group and a substituted or unsubstituted alicyclic hydrocarbon group;

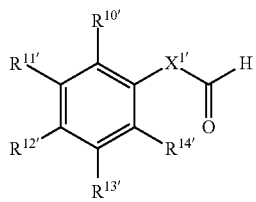
(7)

wherein $R^{10'}$, $R^{11'}$, $R^{12'}$, $R^{13'}$ and $R^{14'}$ each independently represent a hydrogen atom or at least one group selected from the group consisting of an alkyl group having 1 to 10 carbon atoms, an alkoxy group having 1 to 10 carbon atoms, a phenyl group and an amino group; and $X^{1'}$ represents a single bond or a divalent alkyl group having 1 to 10 carbon atoms;

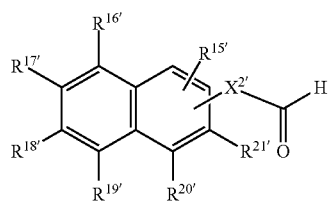
(8)

wherein $R^{15'}$, $R^{16'}$, $R^{17'}$, $R^{18'}$, $R^{19'}$, $R^{20'}$ and $R^{21'}$ each independently represent a hydrogen atom or at least one group selected from the group consisting of an alkyl group having 1 to 10 carbon atoms, an alkoxy group having 1 to 10 carbon atoms, a phenyl group and an amino group; and $X^{2'}$ represents a single bond or a divalent alkyl group having 1 to 10 carbon atoms.

[10]

The method for isomerizing the bis(aminomethyl)cyclohexane according to any one of [7] to [9], wherein the aldehyde comprises:

at least one aliphatic aldehyde selected from the group consisting of formaldehyde, acetaldehyde, isobutyraldehyde, n-decylaldehyde, methacrolein, cinnamaldehyde and glyoxal; and/or at least one aromatic aldehyde selected from the group consisting of benzaldehyde, 4-methylbenzaldehyde, 4-ethylbenzaldehyde, 4-isopropylbenzaldehyde, 4-isobutylbenzaldehyde, 2,4-dimethylbenzaldehyde, 3,4-dimethylbenzaldehyde, 2,4,5-trimethylbenzaldehyde, 2,4,6-trimethylbenzaldehyde and 4-biphenylaldehyde.

[11]

The method for isomerizing the bis(aminomethyl)cyclohexane according to any one of [7] to [10], wherein the ketone comprises at least one selected from the group consisting of an aliphatic ketone, an aromatic ketone, an aliphatic aromatic ketone and a cyclic ketone.

[12]

The method for isomerizing the bis(aminomethyl)cyclohexane according to any one of [7] to [11], wherein the ketone comprises at least one selected from the group consisting of methyl ethyl ketone and acetophenone.

[13]

The method for isomerizing the bis(aminomethyl)cyclohexane according to any one of [1] to [12], wherein the alkali metal-containing compound comprises at least one selected from the group consisting of an alkali metal hydride and an alkali metal amide.

[14]

The method for isomerizing the bis(aminomethyl)cyclohexane according to any one of [1] to [13], wherein the compound comprises at least one selected from the group consisting of metallic sodium, sodium amide and sodium hydride.

[15]

The method for isomerizing the bis(aminomethyl)cyclohexane according to any one of [1] to [14], wherein the bis(aminomethyl)cyclohexane comprises 1,4-bis(aminomethyl)cyclohexane and/or 1,3-bis(aminomethyl)cyclohexane.

[16]

The method for isomerizing the bis(aminomethyl)cyclohexane according to any one of [1] to [15], comprising, during and/or after the isomerization step, an isomer separation step of distilling a trans-isomer of 1,4-bis(aminomethyl)cyclohexane and/or a cis-isomer of 1,3-bis(aminomethyl)cyclohexane.

[17]

The method for isomerizing the bis(aminomethyl)cyclohexane according to any one of [1] to [16], wherein an isomerization reaction temperature of the isomerization step is 100 to 140° C.

[18]

The method according to any one of [1] to [17], wherein, in the isomerization step, bubbling is performed by an inert gas.

[19]

The method according to any one of [1] to [18], wherein, in the isomerization step, a solvent having a boiling point equal to or lower than the isomerization reaction temperature is further used.

[20]

The method for isomerizing the bis(aminomethyl)cyclohexane according to any one of [1] to [19], wherein 1,3-bis(aminomethyl)cyclohexane having a cis-isomer content of 80% or more or 1,4-bis(aminomethyl)cyclohexane having a trans-isomer content of 75% or more is obtained.

[21]

1,3-Bis(aminomethyl)cyclohexane obtained by the method for isomerizing the bis(aminomethyl)cyclohexane according to any one of [1] to [20] and having a cis-isomer content of 80% or more.

[22]

1,4-Bis(aminomethyl)cyclohexane obtained by the method for isomerizing the bis(aminomethyl)cyclohexane according to any one of [1] to [20] and having a trans-isomer content of 75% or more.

Advantageous Effects of Invention

According to this invention, it is possible to provide a method for isomerizing a bis(aminomethyl)cyclohexane, which simply and highly actively realize an isomerization reaction of an industrially important compound, i.e., bis (aminomethyl)cyclohexane, without passing through a high-pressure reaction and a complicated multi-stage process, compared to techniques known in the art.

DESCRIPTION OF EMBODIMENTS

Figure 1:
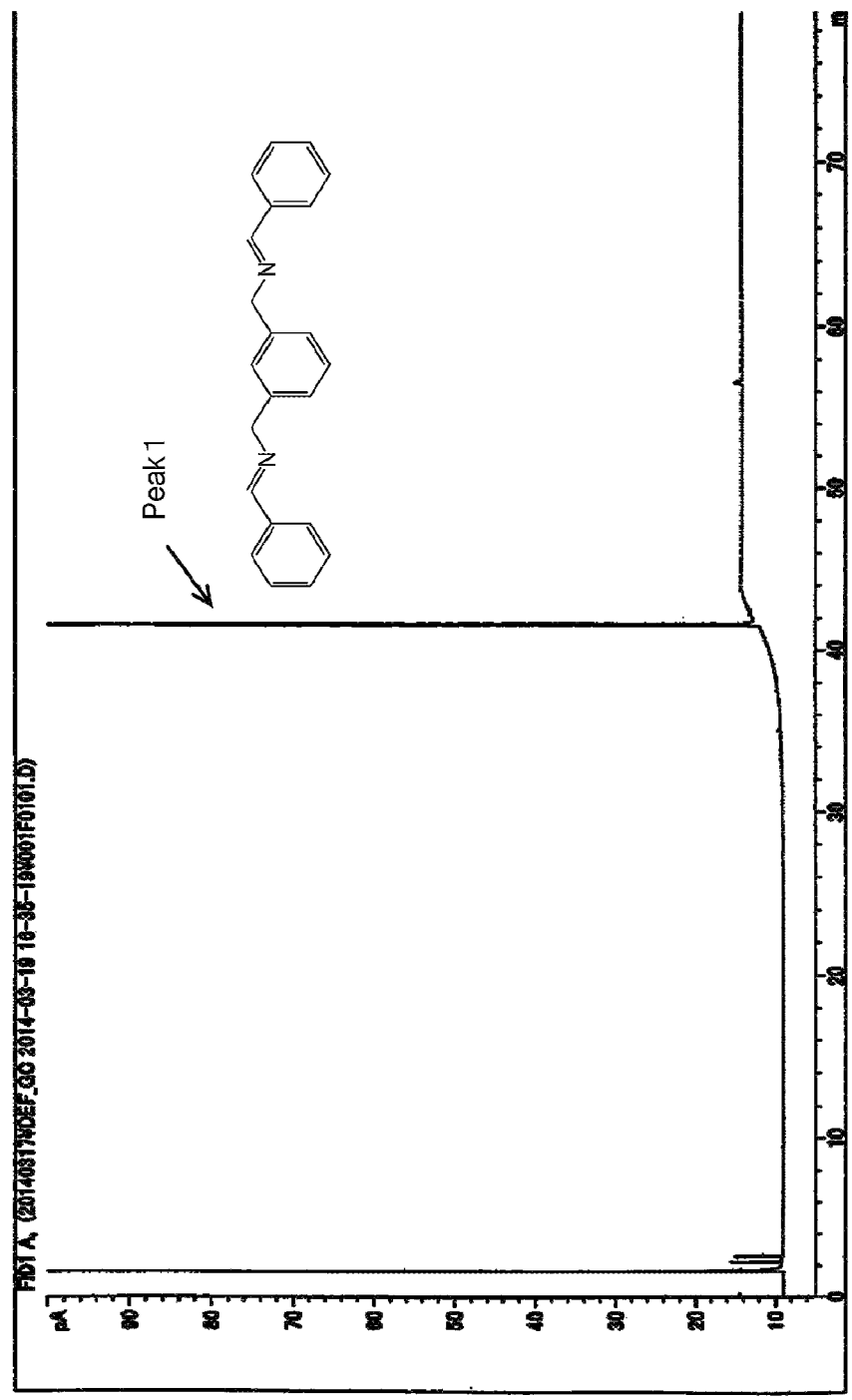
FIG. 1 shows a gas chromatograph of the white powder obtained in Example 3.

Now, embodiments (hereinafter referred to as "the present embodiment") for carrying out the invention will be more specifically described below; however, the present invention is not limited to these and can be modified without departing from the scope of the invention.

Method for isomerizing a bis(aminomethyl)cyclohexane

The isomerization method of a bis(aminomethyl)cyclohexane according to the present embodiment has an isomerization step of isomerizing a bis(aminomethyl)cyclohexane in the presence of an imine compound represented by the following general formula (1) and at least one compound selected from the group consisting of an alkali metal, an alkali metal-containing compound, an alkaline earth metal and an alkaline earth metal-containing compound (hereinafter collectively referred to as an "alkali metal(s)").

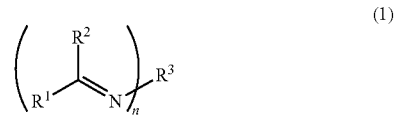

(1)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring); $R^3$ represents a hydrogen atom or an n-valent group selected from the group consisting of substituted or unsubstituted hydrocarbon groups; and n represents an integer of 1 to 10.

In the isomerization method of a bis(aminomethyl)cyclohexane according to the present embodiment, with the above constitution, an active species of an isomerization catalyst can be produced in the isomerization step. Owing to this, an isomerization reaction of a bis(aminomethyl)cyclohexane can be simply and highly actively carried out without passing through a high-pressure reaction and a complicated multi-stage process, compared to techniques known in the art.

[Isomerization Step]

The isomerization step is a step of isomerizing a bis (aminomethyl)cyclohexane in the presence of an imine compound represented by the above general formula (1) and at least one compound selected from the group consisting of an alkali metal, an alkali metal-containing compound, an alkaline earth metal and an alkaline earth metal-containing compound.

The term "isomerizing" refers to converting a trans-isomer of a bis(aminomethyl)cyclohexane to a cis-isomer thereof or converting a cis-isomer of bis(aminomethyl) cyclohexane into a trans-isomer thereof.

The isomerization reaction temperature in the isomerization step is preferably 10 to 200° C., more preferably 80 to 150° C. and further preferably 100 to 140° C. If the isomerization reaction temperature is 10° C. or more, an isomerization reaction tends to be able to more efficiently proceed. If the isomerization reaction temperature is 200° C. or less, a side reaction such as a decomposition reaction and a polymerization reaction can be suppressed and co-production of low-boiling point products and high-boiling point products can be reduced, with the result that the recovery rate of bis(aminomethyl)cyclohexane tends to be more improved. Particularly, if the isomerization reaction temperature is controlled to be 100 to 140° C., a good yield and reaction rate tend to be successfully obtained.

The isomerization reaction time varies depending upon e.g., the use amounts of individual components, reaction conditions and the desired isomer composition; however, the reaction time is preferably 0.50 to 6.0 hours, more preferably 1.0 to 5.0 hours and further preferably 2.0 to 4.0 hours.

The isomerization reaction can be carried out either in the presence or absence of a solvent. As the solvent that can be used, although it is not particularly limited, for example, a solvent inert to a primary amine, an aldehyde, and a ketone, are mentioned. Examples of such a solvent include, but are not particularly limited to, aromatic solvents such as benzene, toluene or xylene; ether solvents such as diethyl ether or tetrahydrofuran; and hydrocarbon solvents such as hexane or heptane. Among them, in order to more effectively promote the isomerization reaction, a solvent having a boiling point equal to or lower than an isomerization reaction temperature is preferable.

As the isomerization reaction atmosphere, although it is not particularly limited, for example, an atmosphere not containing air or active hydrogen such as water or an alcohol, is preferable. If such an atmosphere is employed, an active species of an isomerization catalyst, which is produced by adding an imine compound represented by formula (1) and at least one compound selected from the group consisting of the alkali metals, is rarely inactivated and the reaction efficiency tends to be more improved. Particularly, in order to suppress inactivation of the active species of a catalyst by the reaction with water possibly present in the reaction system, the water content in the reaction system is preferably controlled to be 1000 ppm or less. As a convenient method for preventing contamination with e.g., moisture and air, an isomerization reaction is preferably carried out in an atmosphere of an inert gas such as nitrogen gas and argon gas.

In the isomerization step, bubbling is preferably performed by supplying an inert gas in the reaction system. If so, an isomerization reaction tends to be more effectively promoted.

Bis(aminomethyl)cyclohexane

As the bis(aminomethyl)cyclohexane, although it is not particularly limited, for example, a compound having two aminomethyl groups and a cyclohexane ring is mentioned. More specifically, 1,2-bis(aminomethyl)cyclohexane, 1,3-bis(aminomethyl)cyclohexane and/or 1,4-bis(aminomethyl)cyclohexane are mentioned. Of them, in view of the effect of the present invention, 1,3-bis(aminomethyl)cyclohexane and/or 1,4-bis(aminomethyl)cyclohexane are preferable. As the 1,3-bis(aminomethyl)cyclohexane, a trans-isomer is preferable. As the 1,4-bis(aminomethyl)cyclohexane, a cis-isomer is preferable. According to the method of the present embodiment, any one of the bis(aminomethyl)cyclohexanes can be isomerized.

[Imine Compound]

The imine compound is a compound represented by the above general formula (1). The imine compound is used for forming an active species of an isomerization catalyst for a bis(aminomethyl)cyclohexane. In the above general formula (1), $R^1$ and $R^2$ each independently represent a hydrogen atom or a monovalent group selected from the group consisting of a substituted or unsubstituted hydrocarbon group, a substituted or unsubstituted alkoxy group and an acyl group ($R^1$ and $R^2$ may mutually bind to form a ring). Imine compounds may be used alone or in combination of two or more.

Examples of the substituted or unsubstituted hydrocarbon group represented by each of $R^1$ and $R^2$, include, but are not particularly limited to, a monovalent group selected from the group consisting of an alkyl group, an alkenyl group, an alkynyl group or a substituted or unsubstituted aliphatic hydrocarbon group obtained by substituting one or two or more hydrogen atoms thereof with substituent(s); a cycloalkyl group or a substituted or unsubstituted alicyclic hydrocarbon group obtained by substituting one or two or more hydrogen atoms thereof with substituent(s); and an alkylaryl group, arylalkyl group or a substituted or unsubstituted aromatic hydrocarbon group obtained by substituting one or two or more hydrogen atoms thereof with substituent(s). The aliphatic hydrocarbon groups may be linear or branched.

Examples of the linear aliphatic hydrocarbon group represented by each of $R^1$ and $R^2$ include, but are not particularly limited to, a methyl group, an ethyl group, a propyl group, a butyl group, a pentyl group, a hexyl group, a heptyl group, an octyl group and a decyl group. These linear aliphatic hydrocarbon groups may have a double bond and/or a triple bond.

Examples of the branched aliphatic hydrocarbon group represented by $R^1$ and $R^2$ include, but are not particularly limited to, an isopropyl group, an isobutyl group, a sec-butyl group, a t-butyl group, an isopentyl group, a neopentyl group, a 2-hexyl group, a 2-octyl group and a 2-decyl group. These branched aliphatic hydrocarbon groups may have a double bond and/or a triple bond.

Examples of the alicyclic hydrocarbon group represented by each of $R^1$ and $R^2$ include, but are not particularly limited to, a cyclopropyl group, a cyclobutyl group, a cyclohexyl group, a cyclopentyl group, a cyclooctyl group and a cyclodecyl group. These alicyclic hydrocarbon group may have a double bond and/or a triple bond. Particularly, the alicyclic hydrocarbon group is preferably an alicyclic hydrocarbon group having an amino group.

Examples of the aromatic hydrocarbon group represented by each of $R^1$ and $R^2$ include, but are not particularly limited to, a phenyl group, a naphthyl group, a benzyl group, a methylphenyl group, an ethylphenyl group, a methylnaphthyl group and a dimethylnaphthyl group. Among them, the aromatic hydrocarbon group is preferably a monovalent group selected from the group consisting of a substituted or unsubstituted benzyl group, a substituted or unsubstituted benzal group, a substituted or unsubstituted monovalent phenyl group and a substituted or unsubstituted monovalent naphthyl group.

Examples of the substituted or unsubstituted phenyl group include, but are not particularly limited to, groups represented by the following general formula (4). Examples of the substituted or unsubstituted monovalent naphthyl group include, but are not particularly limited to, groups represented by the following general formula (5).

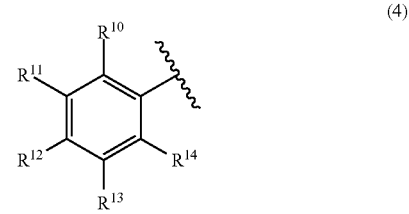

(4)

wherein $R^{10}$, $R^{11}$, $R^{12}$, $R^{13}$ and $R^{14}$ each independently represent a hydrogen atom, an alkyl group having 1 to 10 carbon atoms, an alkoxy group having 1 to 10 carbon atoms, a phenyl group or an amino group.

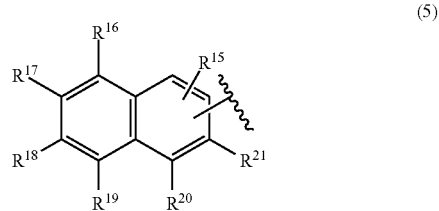

(5)

wherein $R^{15}$, $R^{16}$, $R^{17}$, $R^{18}$, $R^{19}$, $R^{20}$ and $R^{21}$ each independently represent a hydrogen atom, an alkyl group having 1 to 10 carbon atoms, an alkoxy group having 1 to 10 carbon atoms, a phenyl group or an amino group.

The number of carbon atoms of the substituted or unsubstituted hydrocarbon group represented by each of $R^1$ and $R^2$ is preferably 1 to 20, more preferably 1 to 12 and further preferably 1 to 10.

Examples of the substituted or unsubstituted alkoxy group represented by each of $R^1$ and $R^2$ include, but are not particularly limited to, a methoxy group, an ethoxy group, a propoxy group, a butoxy group, a pentyloxy group, a hexyloxy group, an octyloxy group and a decyloxy group. These alkoxy groups may have a double bond and/or a triple bond.

The number of carbon atoms of the substituted or unsubstituted alkoxy group represented by each of $R^1$ and $R^2$ is preferably 1 to 10.

Examples of the substituted or unsubstituted aryloxy group represented by each of $R^1$ and $R^2$ include, but are not particularly limited to, a benzoyloxy group and a naphthyloxy group.

The number of carbon atoms of the substituted or unsubstituted aryloxy group represented by each of $R^1$ and $R^2$ is preferably 6 to 20, more preferably 6 to 12 and further preferably 6 to 10.

Examples of the substituents of the hydrocarbon group and alkoxy group represented by each of $R^1$ and $R^2$ include, but are not particularly limited to, an alkyl group, a carbonyl group, an amino group, an imino group, a cyano group, an azo group, an azide group, a nitro group, an acyl group, an aldehyde group, a cycloalkyl group and an aryl group.

Examples of the acyl group represented by each of $R^1$ and $R^2$ include, but are not particularly limited to, a formyl group, an acetyl group, a propanoyl group, a butanoyl group, a pentanoyl group, a hexanoyl group, an octanoyl group and a benzoyl group. The hydrogen atom of the acyl group may be substituted with a substituent.

The number of carbon atoms of the acyl group represented by each of $R^1$ and $R^2$ is preferably 1 to 10.

Examples of the case where $R^1$ and $R^2$ mutually bind to form a ring, include, but are not particularly limited to, a case where $R^1$ and $R^2$ mutually bind to form an aliphatic ring and a case where $R^1$ and $R^2$ mutually bind to form a heterocyclic ring.

$R^3$ represents a hydrogen atom or an n-valent group selected from the group consisting of substituted or unsubstituted hydrocarbon groups. The reference symbol n represents an integer of 1 to 20, preferably an integer of 1 to 12 and more preferably an integer of 1 to 10.

Examples of the substituted or unsubstituted hydrocarbon group represented by $R^3$ include, but are not particularly limited to, an n-valent group selected from the group consisting of an alkyl group, an alkenyl group, an alkynyl group or a substituted or unsubstituted aliphatic hydrocarbon group obtained by substituting one or two or more hydrogen atoms thereof with substituent(s); a cycloalkyl group or a substituted or unsubstituted alicyclic hydrocarbon group obtained by substituting one or two or more hydrogen atoms thereof with substituent(s); and an alkylaryl group, arylalkyl group, a benzal group or a substituted or unsubstituted aromatic hydrocarbon group obtained by substituting one or two or more hydrogen atoms thereof with substituent(s). The aliphatic hydrocarbon groups may be linear or branched.

Examples of the linear aliphatic hydrocarbon group represented by $R^3$ include, but are not limited to, a methyl group, an ethyl group, a propyl group, a butyl group, a pentyl group, a hexyl group, a heptyl group, an octyl group and a decyl group. These linear aliphatic hydrocarbon groups may have a double bond and/or a triple bond.

Examples of the branched aliphatic hydrocarbon group represented by $R^3$ include, but are not limited to, an isopropyl group, an isobutyl group, a sec-butyl group, a t-butyl group, an isopentyl group, a neopentyl group, a 2-hexyl group, a 2-octyl group and a 2-decyl group. These branched aliphatic hydrocarbon groups may have a double bond and/or a triple bond.

Examples of the alicyclic hydrocarbon group represented by $R^3$ include, but are not particularly limited to, a cyclopropyl group, a cyclobutyl group, a cyclohexyl group, a cyclopentyl group, a cyclooctyl group, a cyclodecyl group and a cyclohexanedimethylene group. These cyclic aliphatic hydrocarbon groups may have a double bond and/or a triple bond. Particularly, the alicyclic hydrocarbon group is preferably an alicyclic hydrocarbon group having an amino group.

Examples of the aromatic hydrocarbon group represented by $R^3$ include, but are not particularly limited to, a phenyl group, a phenylene group, a naphthyl group, a naphthylene group, a benzyl group, a methylphenyl group, a methylphenylene group, an ethylphenyl group, an ethylphenylene group, a methylnaphthyl group, a methylnaphthylene group, a dimethylnaphthyl group, a dimethylnaphthylene group and a xylylene group.

The number of carbon atoms of the substituted or unsubstituted hydrocarbon group represented by $R^3$ is preferably 1 to 20, more preferably 1 to 12 and further preferably 1 to 10.

As the substituents of a hydrocarbon group represented by $R^3$, although it is not particularly limited, for example, the same substituents as defined in $R^1$ and $R^2$ are mentioned.

As the imine compound represented by the general formula (1), although it is not particularly limited, for example, a compound represented by the following general formula (2) and/or a compound represented by the following general formula (3) are preferable. If such a compound is used, production of by-products after isomerization can be suppressed and the amount of by-products to be separated can be decreased, with the result that a highly purified bis(aminomethyl)cyclohexane tends to be successfully and easily obtained.

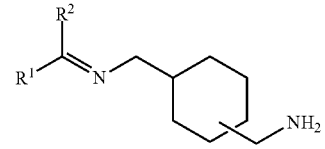

(2)

wherein $R^1$ and $R^2$ each independently represent a hydrogen atom, or a monovalent group selected from the group consisting of a substituted or unsubstituted hydrocarbon group, a substituted or unsubstituted alkoxy group and an acyl group ($R^1$ and $R^2$ may mutually bind to form a ring).

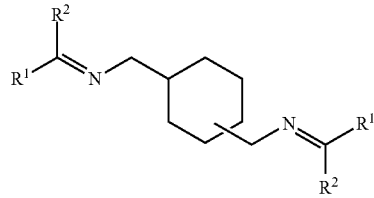

(3)

wherein $R^1$ and $R^2$ each independently represent a hydrogen atom, or a monovalent group selected from the group consisting of a substituted or unsubstituted hydrocarbon group, a substituted or unsubstituted alkoxy group and an acyl group ($R^1$ and $R^2$ may mutually bind to form a ring).

In the above general formulas (2) and (3), $R^1$ and $R^2$ are the same as defined in the above general formula (1).

As the imine compound, not only a compound available as a reagent but also a compound obtained by organic synthesis can be used. Examples of the compound available as a reagent include, but are not particularly limited to, benzylidene aniline and N-benzylidene-tertiary butylamine. Examples of the compound obtained by organic synthesis include, but are not particularly limited to, imine compounds described in Chem. Rev., 1963, 63(5), pp 489-510 The CHEMISTRY OF IMINES, Table I to Table VII, which have a substituent containing a functional group inert to an alkali metal, an alkali metal amide, an alkali metal hydride, an alkaline earth metal or an alkaline earth metal hydride. These may be used without any purification.

The use amount of imine compound, although it is not particularly limited, is preferably 0.10 to 10 mol % relative to bis(aminomethyl)cyclohexane (100 mol %) and more preferably 0.50 to 4.0 mol %. If the use amount of imine compound is 0.10 mol % or more, the isomerization reaction tends to more quickly and smoothly proceed. In addition, if the use amount of imine compound falls within the above range, a side reaction such as a polymerization reaction between bis(aminomethyl)cyclohexane molecules can be suppressed, with the result that the yield of a desired isomer is improved and catalyst cost tends to be successfully suppressed to a minimum. In the isomerization method of the present embodiment, even if the use amount of imine compound is the above catalyst amount, the reaction can efficiently proceed.

(Method for Synthesizing Imine Compound)

The imine compound is preferably obtained by dehydration condensation between a primary amine and an aldehyde and/or a ketone and more preferably dehydration condensation between a bis(aminomethyl)cyclohexane and an aldehyde and/or a ketone. Such an imine compound may be added in the reaction system of the isomerization method of the present embodiment or may be produced in the reaction system.

Particularly, for isomerizing 1,4-bis(aminomethyl)cyclohexane, an imine compound obtained by dehydration condensation between 1,4-bis(aminomethyl)cyclohexane and an aldehyde or a ketone is more preferably used. If the imine compound obtained by the dehydration condensation reaction between 1,4-bis(aminomethyl)cyclohexane and an aldehyde or a ketone is used, the amount of compounds to be separated decreases and the purity of 1,4-bis(aminomethyl)cyclohexane becomes to be easily improved.

For isomerizing 1,3-bis(aminomethyl)cyclohexane, an imine compound obtained by a dehydration condensation reaction between 1,3-bis(aminomethyl)cyclohexane and an aldehyde or a ketone is more preferably used. If the imine compound obtained by the dehydration condensation reaction between 1,3-bis(aminomethyl)cyclohexane and an aldehyde or a ketone is used, the amount of compounds to be separated decreases and the purity of 1,3-bis(aminomethyl)cyclohexane becomes to be easily improved.

The above dehydration condensation reaction can be carried out in the presence or absence of a catalyst. The above dehydration condensation reaction can be also carried out in the presence or absence of a solvent. As the solvent that can be used herein, although it is not particularly limited, for example, solvents inert to a primary amine, an aldehyde and a ketone, are mentioned. Examples of the solvents include, but are not particularly limited to, aromatic solvents such as benzene, toluene or xylene; ether solvents such as diethyl ether or tetrahydrofuran; and hydrocarbon solvents such as hexane or heptane.

As a method for a dehydration condensation reaction, although it is not particularly limited, for example, specifically, an azeotropic dehydration method using a dean stark apparatus is mentioned. In this method, an imine compound can be easily obtained by azeotropically dehydrating components in a benzene solvent. In the case where a dehydration condensation reaction is carried out in the absence of a solvent, the dehydration condensation can easily progress by removing water from the reaction system by e.g., a distillation operation.

In the case where an imine compound is prepared in an isomerization reaction system, the isomerization method of the present embodiment may have, before and/or after the isomerization step, a dehydration condensation step in which a bis(aminomethyl)cyclohexane is mixed with an aldehyde and/or a ketone and subjected to a dehydration condensation, thereby obtaining an imine compound in the reaction system.

If the isomerization method has the dehydration condensation step, a bis(aminomethyl)cyclohexane can be isomerized by adding an alkali metal in the reaction system, even though an imine compound obtained through the dehydration condensation between an aldehyde or ketone and a primary amine is not isolated.

If the isomerization method has the dehydration condensation step, an aldehyde or a ketone, which is industrially easily and inexpensively available, can be used as a raw material for a catalyst, and a bis(aminomethyl)cyclohexane can be industrially advantageously isomerized without using e.g., a noble metal catalyst of high cost. Thus, the dehydration condensation step has extremely high industrial significance.

(Primary Amine)

As the primary amine, although it is not particularly limited, for example, a compound generally available and providing an imine compound having a substituent containing a functional group inert to an alkali metals are mentioned. The primary amine may be used alone or in combination (of two or more); however, a single primary amine is preferably used alone in order to simplify the industrial process.

Examples of the primary amine include, but are not particularly limited to, methylamine, ethylamine, propylamine, isopropylamine, butylamine, isobutylamine, tert-butylamine, benzylamine, methylbenzylamine, dimethylbenzylamine, aniline, meta-xylylenediamine, paraxylylenediamine, cyclohexylamine, 1,3-bis(aminomethyl)cyclohexane or 1,4-bis(aminomethyl)cyclohexane, isophoronediamine, o-phenylenediamine, m-phenylenediamine, p-phenylenediamine, phenethylamine, diaminodiphenylmethane, methanediamine, ethanediamine, propanediamine, butanediamine, pentanediamine and hexanediamine.

Among them, a bis(aminomethyl)cyclohexane is preferable. If a bis(aminomethyl)cyclohexane, which is a target compound to be isomerized, is used, an isomerization reaction can be carried out without using another amine and the resultant bis(aminomethyl)cyclohexane tends to be more simply purified.

(Aldehyde)

As the aldehyde, although it is not particularly limited, for example, a compound generally available and having a substituent containing a functional group inert to an alkali metal, is mentioned. As such an aldehyde, although it is not particularly limited, for example, at least one selected from the group consisting of an aliphatic aldehyde represented by the following general formula (6), an aromatic aldehyde represented by the following general formula (7) and an aromatic aldehyde represented by the following general formula (8) is mentioned. If such a compound is used, the ratio of a trans-isomer or a cis-isomer in the resultant isomers and an isomerization yield tend to be improved.

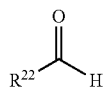

(6)

wherein $R^{22}$ represents a hydrogen atom or a monovalent substituent selected from the group consisting of a substituted or unsubstituted aliphatic hydrocarbon group and a substituted or unsubstituted alicyclic hydrocarbon group.

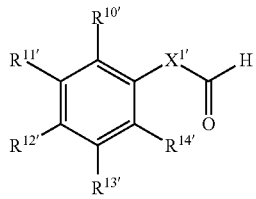

(7)

wherein $R^{10'}$, $R^{11'}$, $R^{12'}$, $R^{13'}$ and $R^{14'}$ each independently represent a hydrogen atom or at least one group selected from the group consisting of an alkyl group having 1 to 10 carbon atoms, an alkoxy group having 1 to 10 carbon atoms, a phenyl group and an amino group; and $X^{1'}$ represents a single bond or an a divalent alkyl group having 1 to 10 carbon atoms.

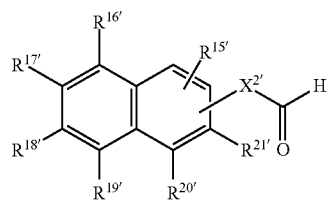

(8)

wherein $R^{15'}$, $R^{16'}$, $R^{17'}$, $R^{18'}$, $R^{19'}$, $R^{20'}$ and $R^{21'}$ each independently represent a hydrogen atom or at least one group selected from the group consisting of an alkyl group having 1 to 10 carbon atoms, an alkoxy group having 1 to 10 carbon atoms, a phenyl group and an amino group; and $X^{2'}$ represents a single bond or a divalent alkyl group having 1 to 10 carbon atoms.

As the above aldehyde, although it is not particularly limited, for example, formaldehyde, an aliphatic aldehyde and an aromatic aldehyde are mentioned. If such a compound is used, the ratio of a trans-isomer or a cis-isomer in the resultant isomers and the isomerization yield tend to be improved. Aldehydes may be used alone or in combination (of two or more); however, a single aldehyde is preferably used alone in order to simplify the industrial process.

Examples of the aliphatic aldehyde include, but are not particularly limited to, acetaldehyde, propionaldehyde, 4-isopropylaldehyde, isobutyraldehyde, n-butyraldehyde, n-valeraldehyde, isovaleraldehyde, pivalaldehyde, n-hexylaldehyde, n-heptylaldehyde, n-octylaldehyde, n-nonylaldehyde, n-decylaldehyde, acrolein, methacrolein, 2-methylpentanal, crotonaldehyde, cinnamaldehyde, phenylacetaldehyde, p-methylphenylacetaldehyde, glyoxal, glutaraldehyde, hydroxypivalaldehyde, (+)-citronellal and (−)-citronellal. Among them, at least one selected from the group consisting of acetaldehyde, isobutyraldehyde, n-decylaldehyde, methacrolein, cinnamaldehyde and glyoxal, is preferable. If such a compound is used, the ratio of a trans-isomer or a cis-isomer in the resultant isomers and the isomerization yield tend to be improved.

Examples of the aromatic aldehyde include, but are not particularly limited to, benzaldehyde, 2-methylbenzaldehyde, 3-methylbenzaldehyde, 4-methylbenzaldehyde, 2-ethylbenzaldehyde, 3-ethylbenzaldehyde, 4-ethylbenzaldehyde, 2-propylbenzaldehyde, 3-propylbenzaldehyde, 4-propylbenzaldehyde, 2-isopropylbenzaldehyde, 3-isopropylbenzaldehyde, 4-isopropylbenzaldehyde, 4-biphenylaldehyde, 2-butylbenzaldehyde, 3-butylbenzaldehyde, 4-butylbenzaldehyde, 2-tert-butylbenzaldehyde, 3 tertiary butylbenzaldehyde, 4-tertiary butylbenzaldehyde, 2-phenylbenzaldehyde, 3-phenylbenzaldehyde, 4-phenylbenzaldehyde, 2,3-dimethylbenzaldehyde, 2,4-dimethylbenzaldehyde, 2,5-dimethylbenzaldehyde, 2,6-dimethylbenzaldehyde, 3,4 dimethylbenzaldehyde, 3,5-dimethylbenzaldehyde, 2,4,5-trimethylbenzaldehyde, 2,4,6-trimethylbenzaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 1-naphthaldehyde, 2-naphthaldehyde and 3-naphthaldehyde. Among them, at least one compound selected from the group consisting of benzaldehyde, 4-methylbenzaldehyde, 4-ethylbenzaldehyde, 4-isopropylbenzaldehyde, 2,4-dimethylbenzaldehyde, 3,4-dimethylbenzaldehyde, 2,4,5-trimethylbenzaldehyde, 2,4,6-trimethylbenzaldehyde, 4-isobutylbenzaldehyde and 4-biphenylaldehyde, is preferable. If such a compound is used, the ratio of a trans-isomer or a cis-isomer in the resultant isomers and the isomerization yield tend to be improved.

The use amount of aldehyde relative to a bis(aminomethyl)cyclohexane (100% by mole) is preferably 0.10 to 10 mol %, more preferably 0.20 to 5.0 mol % and further preferably 0.50 to 2.0 mol %. If the use amount of aldehyde falls within the above range, the isomerization reaction more quickly and smoothly proceeds and a side reaction such as a polymerization reaction between bis(aminomethyl)cyclohexane molecules can be suppressed, with the result that the yield of a desired isomer is improved and catalyst cost tends to be successfully suppressed to a minimum.

(Ketone)

As the ketone, although it is not particularly limited, for example, a compound generally available and providing a compound having a substituent containing a functional group inert to an alkali metal, is mentioned. As such a ketone, although it is not particularly limited, for example, at least one selected from the group consisting of an aliphatic ketone, an aromatic ketone, an aliphatic aromatic ketone and a cyclic ketone, is mentioned. If such a compound is used, the ratio of a trans-isomer or a cis-isomer in the resultant isomers and the isomerization yield tend to be improved. Ketones may be used alone or in combination (of two or more); however, a single ketone is preferably used alone in order to simplify the industrial process.

Examples of the aliphatic ketone include, but are not particularly limited to, acetone, methyl ethyl ketone, diethyl ketone, methyl propyl ketone, methyl isobutyl ketone, ethyl propyl ketone, ethyl isobutyl ketone and dipropyl ketone.

Examples of the aromatic ketone include, but are not particularly limited to, benzophenone.

Examples of the aliphatic aromatic ketone include, but are not particularly limited to, acetophenone.

Examples of the cyclic ketone include, but are not particularly limited to, cyclohexanone.

Among them, at least one ketone selected from the group consisting of methyl ethyl ketone and acetophenone, is preferable. If such a compound is used, the ratio of a trans-isomer or a cis-isomer in the resultant isomers and the isomerization yield tend to be improved.

The use amount of ketone relative to a bis(aminomethyl) cyclohexane (100% by mole) is preferably 0.10 to 10 mol %, more preferably 0.20 to 5.0 mol % and further preferably 0.50 to 2.0 mol %. If the use amount of ketone falls within the above range, the isomerization reaction more quickly and smoothly proceeds and a side reaction such as a polymerization reaction between bis(aminomethyl)cyclohexane molecules can be suppressed, with the result that the yield of a desired isomer is further improved and catalyst cost tends to be successfully suppressed to a minimum.

[Compound]

The compound to be used in the isomerization method of the present embodiment is at least one compound selected from the group consisting of an alkali metal, an alkali metal-containing compound, an alkaline earth metal and an alkaline earth metal-containing compound. These compounds can proceed the isomerization reaction, in the isomerization method of the present embodiment. These compounds may be used alone or in combination (of two or more).

Among them, at least one selected from the group consisting of an alkali metal, an alkali metal hydride and an alkali metal amide is preferable as the compound, and more specifically, at least one compound selected from the group consisting of a metallic sodium, a sodium amide and a sodium hydride is preferably included. If such a compound is used, the ratio of a trans-isomer or a cis-isomer in the resultant isomers and the isomerization yield tend to be improved.

Examples of the alkali metals include, but are not particularly limited to, a metallic sodium, a metallic lithium and a metallic potassium.

Examples of the alkali metal-containing compounds include, but are not particularly limited to, an alkali metal hydride, an alkali metal amide, a basic oxide and an alkali metal alkoxide. If such a compound is used, the ratio of a trans-isomer or a cis-isomer in the resultant isomers and the isomerization yield tend to be improved. Among them, at least one selected from the group consisting of an alkali metal hydride and an alkali metal amide, is preferable. Examples of the alkali metal hydride herein include, but are not particularly limited to, sodium hydride, lithium hydride, potassium hydride, lithium aluminum hydride and sodium boron hydride. Examples of the alkali metal amide include, but are not particularly limited to, sodium amide, lithium amide, potassium amide, lithium diisopropylamide and sodium bis(trimethylsilyl)amide. Examples of the basic oxide include, but are not particularly limited to, lithium oxide, sodium oxide, potassium oxide, cesium oxide, magnesium oxide, calcium oxide, strontium oxide and barium oxide. Examples of the alkali metal alkoxide include, but are not particularly limited to, potassium-tert-butoxide.

Examples of the alkaline-earth metal include, but are not particularly limited to, metallic magnesium and metallic calcium.

Examples of the alkaline-earth metal-containing compound include, but are not particularly limited to, an alkaline earth metal hydride. Examples of the alkaline earth metal hydride include, but are not particularly limited to, calcium hydride and magnesium hydride.

The use amount of compound as mentioned above relative to a bis(aminomethyl)cyclohexane (100% by mole) is, but are not particularly limited to, preferably 0.10 to 10 mol %, more preferably 0.2 to 5.0 mol % and further preferably 0.5 to 2 mol %. If the use amount of compound as mentioned above falls within the above range, the isomerization reaction tends to more efficiently proceed.

[Purification Step]

The isomerization method of the present embodiment may have a purification step such as a catalyst component removal step of removing a catalyst component, a low boiling-point component removal step of removing low boiling-point components, a high boiling-point component removal step for removing high boiling-point components and an isomer separation step for distilling an isomer of a bis(aminomethyl)cyclohexane. Note that the term "catalytic component" herein more specifically refers to an imine compound and an alkali metal. The term "low boiling-point components" refer to components having lower boiling points than those of isomers of a bis(aminomethyl)cyclohexane. The term "high boiling-point components" refer to components having higher boiling points than those of isomers of a bis(aminomethyl)cyclohexane.

Note that the catalyst component removal step, low boiling-point component removal step, high boiling-point component removal step and isomer separation step may be carried out in a random order.

[Catalyst Component Removal Step]

The catalyst component removal step is a step of removing a catalytic component present in a reaction mixture after an isomerization step. If the catalyst component removal step is carried out, a side reaction can be further suppressed from proceeding in the purification step. As the method of removing the catalyst, although it is not particularly limited, for example, thin-film distillation can be used. The catalytic component to be separated herein can be inactivated and then separated or can be separated in an active state. The catalytic component separated in an active state can be used again as a catalyst for an isomerization reaction.

[Low Boiling-Point Component Removal Step]

The low boiling-point component removal step is a step of removing low boiling-point components having lower boiling points than those of isomers of a bis(aminomethyl) cyclohexane during or after an isomerization step. If the low boiling-point component removal step is carried out, the yield of the isomer tends to be more improved. As the method of removing the low boiling-point components, although it is not particularly limited, for example, a method of performing distillation at a temperature equal to or lower than the boiling points of isomers of a bis(aminomethyl) cyclohexane to remove low boiling-point components from the reaction mixture, is mentioned.

[High Boiling-Point Component Removal Step]

The high boiling-point component removal step is a step of removing high boiling-point components having higher boiling points than those of isomers of a bis(aminomethyl) cyclohexane after an isomerization step. As the method of removing the high boiling-point components, although it is not particularly limited, for example, a method of distilling the isomers of a bis(aminomethyl)cyclohexane from the reaction mixture in the following isomer separation step, and thereafter, removing high boiling-point components remaining in the reaction mixture, is mentioned.

[Isomer Separation Step]

The isomer separation step is a step of distilling a trans-isomer of 1,4-bis(aminomethyl)cyclohexane and/or a cis-isomer of 1,3-bis(aminomethyl)cyclohexane during or after an isomerization step. If the isomer separation step is carried out, the yield of the isomer tends to be more improved.

As described above, the isomers of a bis(aminomethyl) cyclohexane obtained by the method of the present embodiment can be isolated by a general method such as distillation. If distillation is carried out, isomerization is preferably carried out while separating isomerized bis(aminomethyl) cyclohexanes. In this manner, a bis(aminomethyl)cyclohexane containing isomers in a high concentration which is equal to or higher than that in the equivalent composition can be produced.

Particularly, in the case where 1,4-bis(aminomethyl)cyclohexane is used as a bis(aminomethyl)cyclohexane, isomerization of the invention is preferably carried out while separating 1,4-bis(aminomethyl)cyclohexane having a trans-isomer in a high content. In this manner, 1,4-bis(aminomethyl)cyclohexane containing a trans-isomer in a high concentration which is equal to or higher than that in the equivalent composition can be produced.

In the case where 1,3-bis(aminomethyl)cyclohexane is used as a bis(aminomethyl)cyclohexane, isomerization of the invention is preferably carried out while separating 1,3-bis(aminomethyl)cyclohexane having a cis-isomer in a high content. In this manner, 1,3-bis(aminomethyl)cyclohexane containing a cis-isomer in a high concentration which is equal to or higher than that in the equivalent composition can be produced.

Note that distillation conditions such as distillation temperature can be appropriately controlled depending upon the desired isomer.

In the isomerization method of the present embodiment, if 1,4-bis(aminomethyl)cyclohexane is used as a bis(aminomethyl)cyclohexane, the trans-isomer content in the resulting product is preferably 75% or more and more preferably 80% or more. Now, the term "%" used herein refers to mol %.

In the isomerization method of the present embodiment, if 1,3-bis(aminomethyl)cyclohexane is used as a bis(aminomethyl)cyclohexane, the cis-isomer content in the resulting product is 80% or more. Now, the term "%" used herein refers to mol %.

1,3-Bis(aminomethyl)cyclohexane 1,3-Bis(aminomethyl)cyclohexane of the present embodiment is obtained by the above method and has a cis-isomer content of 80% or more.

1,4-Bis(aminomethyl)cyclohexane 1,4-Bis(aminomethyl)cyclohexane of the present embodiment is obtained by the above method and has a trans-isomer content of 75% or more.

Now, a means for carrying out the isomerization method of the present embodiment will be described; however, the isomerization method of the present embodiment is not limited to the followings.

As the first aspect, the isomerization method of the present embodiment can be carried out by mixing an imine compound, an alkali metal and a bis(aminomethyl)cyclohexane in a reactor. The reactor may have a heating means for heating the reactor, a stirring means for stirring the mixture in the reactor and a gas supply means for bubbling the mixture in the reactor.

To a reactor, an imine compound, an alkali metal, and a bis(aminomethyl)cyclohexane may be added in a random manner. Two components are selected from an imine compound, an alkali metal and bis(aminomethyl)cyclohexane and mixed in advance, and then, the mixture may be added. Alternatively, a mixture of an imine compound, an alkali metal or a bis(aminomethyl)cyclohexane and a solvent may be added.

As an addition means for adding an imine compound, an alkali metal and a bis(aminomethyl)cyclohexane, a means which can add these compounds at a time in a reactor or a means which can continuously add them dropwise may be employed.

The reactor may have a gas supply means and a gas exhaust means for controlling the atmosphere within the reactor. The reactor may be constituted so as to reflux a solvent. The reactor may be designed for a batch reaction or a continuous reaction.

As the second aspect, a first reactor for producing an imine compound by supplying a primary amine, an aldehyde and/or a ketone thereto and a second reactor for carrying out an isomerization reaction may be employed. In this case, the second reactor is designed to communicate with the first reactor such that the imine compound produced is supplied thereto. The first reactor and/or the second reactor may have a dehydration means (for example, a dean stark apparatus, a distillation apparatus) for removing water from the reaction system. Note that in the case where a bis(aminomethyl) cyclohexane is used as the amine, the raw materials to be supplied to the second reactor may contain an imine compound and the bis(aminomethyl)cyclohexane. Other structures can be the same as defined in the first aspect.

As the third aspect, a reactor for mixing an imine compound, an alkali metal and a bis(aminomethyl)cyclohexane and a distiller communicating with the reactor, may be employed. In this case, the reactor and the distiller may be integrated into one body. Other structures can be the same as defined in the first aspect.

EXAMPLES

Now, the present invention will be more specifically described by way of Examples and Comparative Examples; however, the present invention is not limited to these Examples.

[Isomer Composition]

Isomer compositions (cis/trans ratio) were analyzed by a gas chromatographic apparatus equipped with a capillary column, CP-Volamine manufactured by Valian.

The trans-isomer of 1,4-bis(aminomethyl)cyclohexane has a lower boiling point than the cis-isomer thereof. The isomer first detected by gas chromatography is the trans-isomer and the cis-isomer is detected thereafter. The cis-isomer of 1,3-bis(aminomethyl)cyclohexane has a lower boiling point than the trans-isomer thereof. The isomer first detected by gas chromatography is the cis-isomer and the trans-isomer is detected thereafter. The ratio of the trans-isomer was calculated in accordance with the expression:

Area value of trans-isomer/(area value for cis-isomer+area value for trans-isomer)×100.

The ratio of the cis-isomer was calculated by the ratio to the trans-isomer from 100.

[Isomerization Yield]

Isomerization yields were calculated by the internal standard method of the above gas chromatography analysis.

Isomerization yield (%)=(bis(aminomethyl)cyclohexane after the isomerization reaction)/(bis(aminomethyl)cyclohexane before isomerization reaction)×100

[Analysis of Imine Compound]

Imine compounds were analyzed by a gas chromatographic apparatus equipped with a capillary column, HP-1, manufactured by Agilent Technologies.

[Raw Materials]

Imine compounds, aldehydes, ketones, sodium amide, sodium hydride and sodium used herein were reagent grades. 1,4-Bis(aminomethyl)cyclohexane used herein was nuclear-hydrogenated by using Ru-alumina in the presence of paraxylylenediamine as a catalyst, in accordance with a technique known in the art (for example, Japanese Patent Laid-Open No. 50-126638) and purified by distillation. 1,3-Bis(aminomethyl)cyclohexane used herein was a reagent grade (manufactured by Tokyo Chemical Industry Co., Ltd.).

Example 1

Imine Compound: Benzylidene Aniline 1,4-Bis(aminomethyl)cyclohexane (cis/trans=60/40)(100 g) and 3.1 g of benzylidene aniline (represented by the following formula (9) and manufactured by Tokyo Chemical Industry Co., Ltd.) were weighed and placed in a 300-mL flask, and then, sodium amide (2.0 g) was added under an argon gas stream. An isomerization reaction was carried out at 120° C. for 4 hours. The isomer composition (cis/trans) after the isomerization reaction was 19/81 and the isomerization yield was 85%.

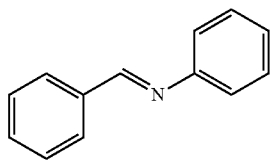

(9)

Example 2

Imine compound: N-benzylidene-t-butylamine 1,4-Bis(aminomethyl)cyclohexane (cis/trans=60/40) (100 g) and 2.7 g of N-benzylidene-t-butylamine (represented by the following formula (10) and manufactured by Sigma-Aldrich) were weighed and placed in a 300-mL flask, and then, sodium amide (2.0 g) was added under an argon gas stream. An isomerization reaction was carried out at 120° C. for 4 hours. The isomer composition (cis/trans) after the isomerization reaction was 18/82 and the isomerization yield was 86%.

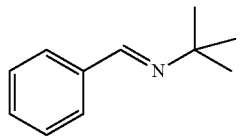

(10)

Example 3

Imine Compound: Condensate of Metaxylylenediamine and Benzaldehyde

Figure 2:
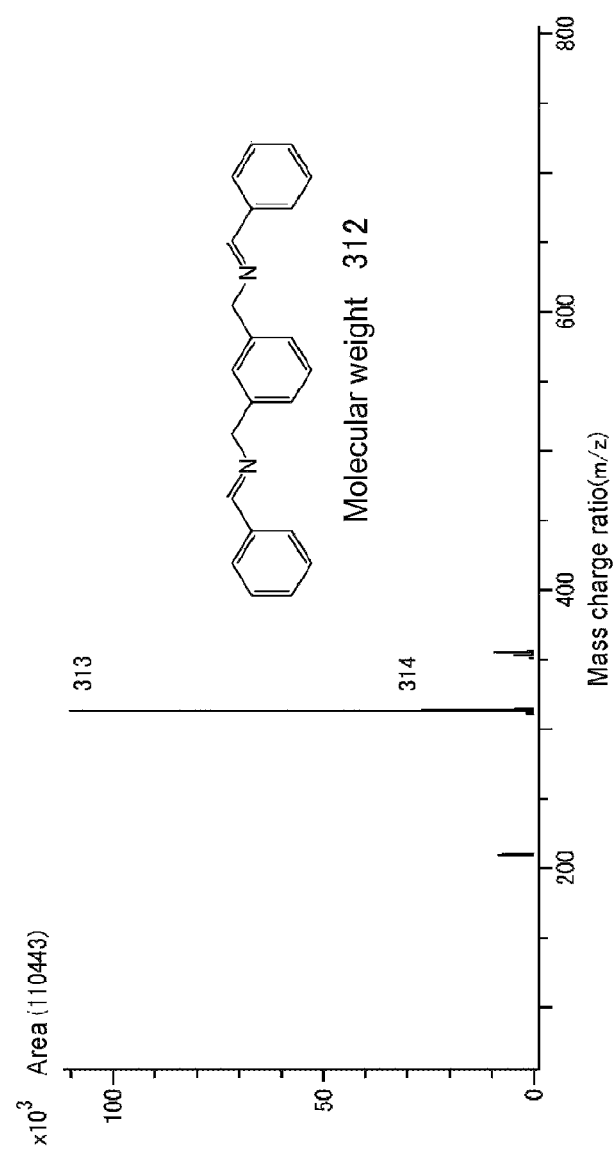
FIG. 2 shows a CI-MS spectrum of peak 1 of the gas chromatograph of Example 3.
Figure 3:
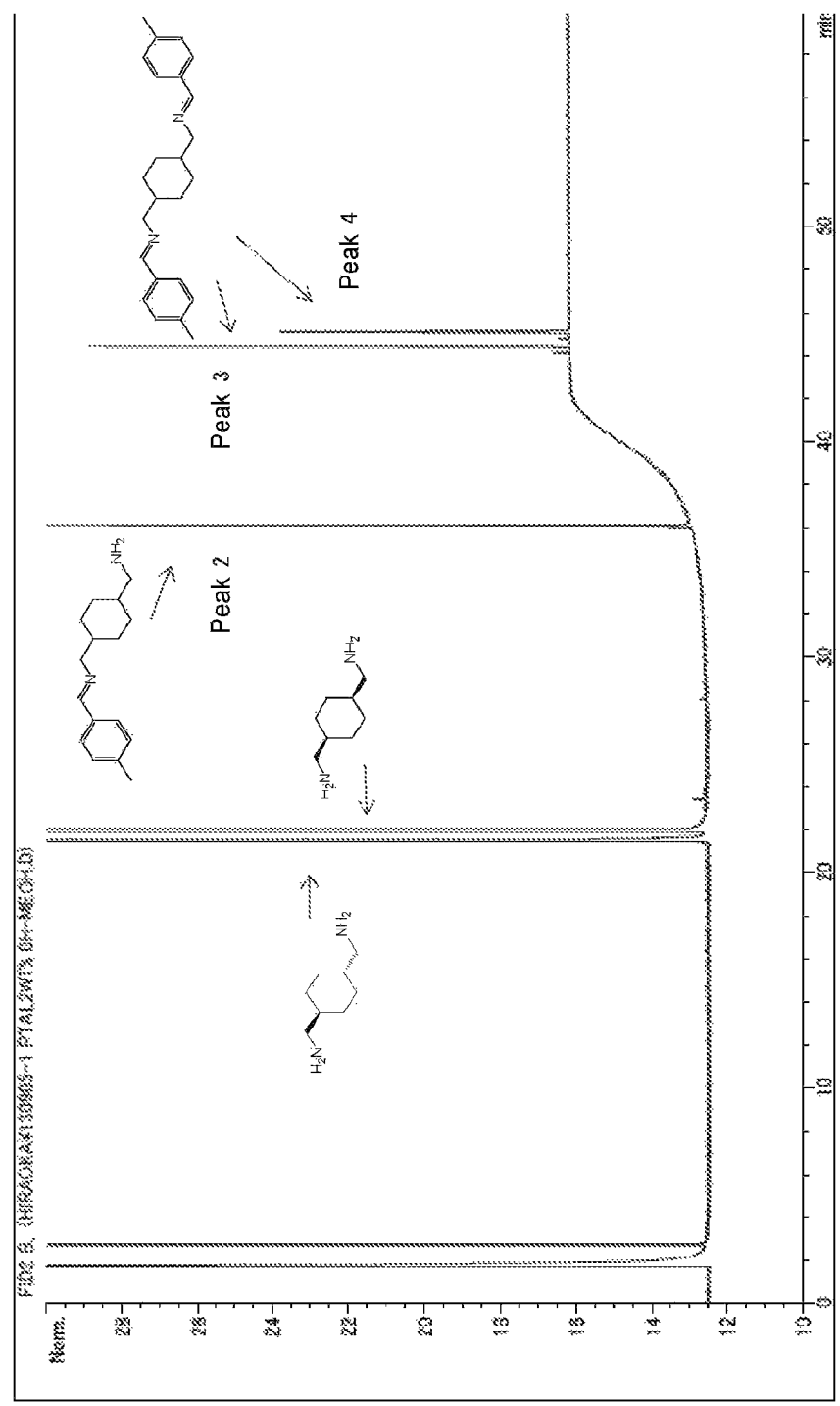
FIG. 3 shows a gas chromatograph of the reaction solution obtained in Example 4.
Figure 4:
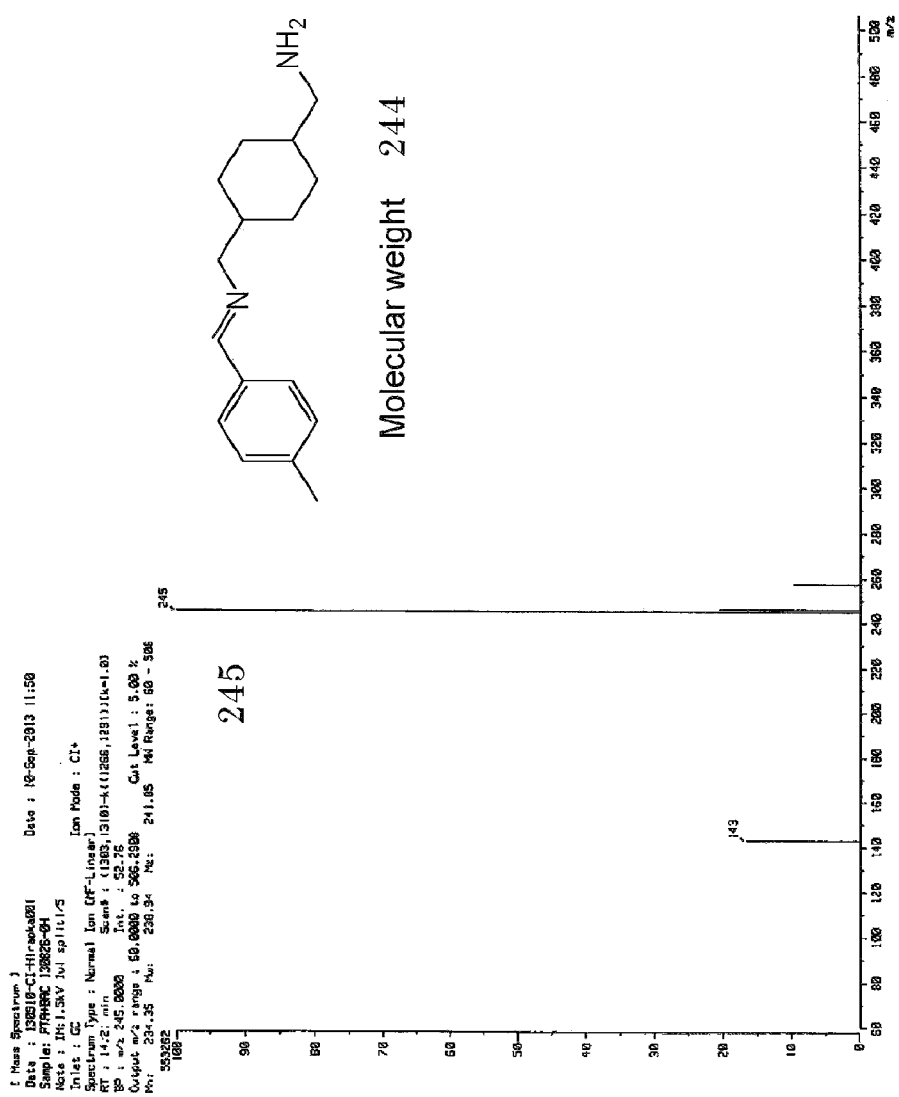
FIG. 4 shows a CI-MS spectrum of peak 2 of the gas chromatograph of Example 4.
Figure 5:
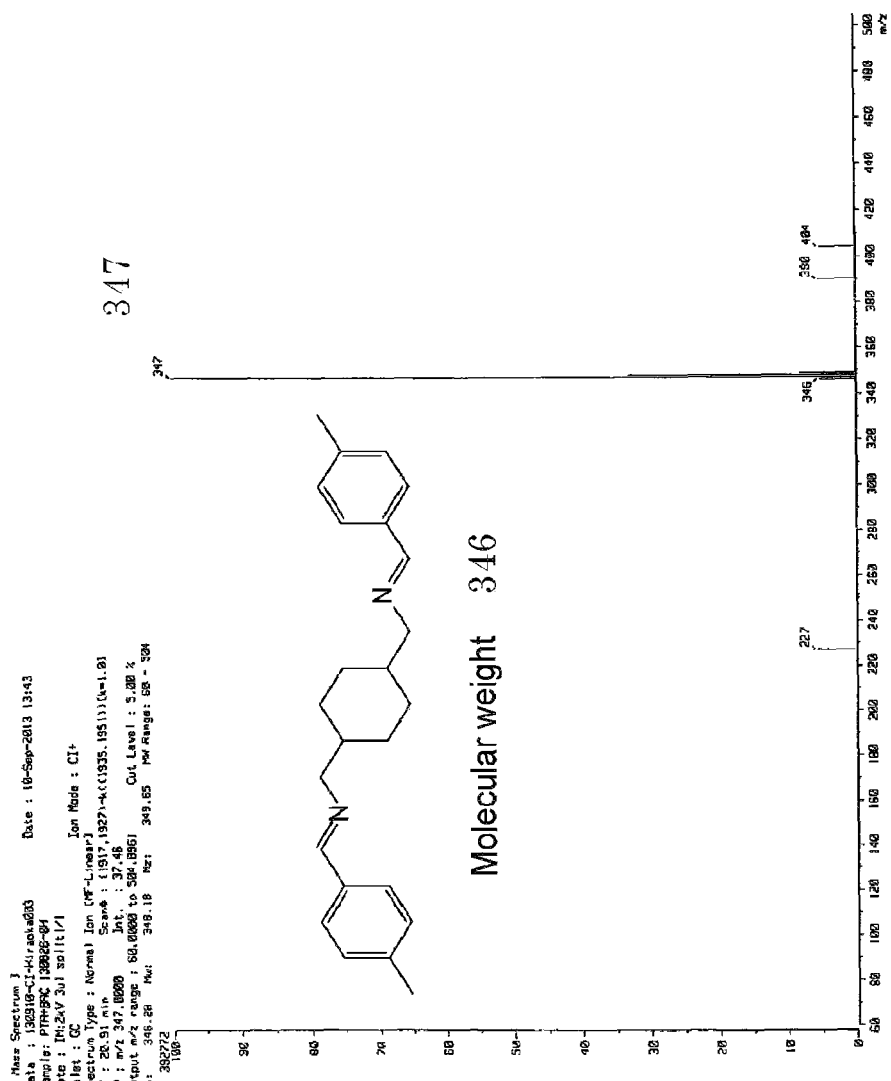
FIG. 5 shows a CI-MS spectrum of peak 3 of the gas chromatograph of Example 4.
Figure 6:
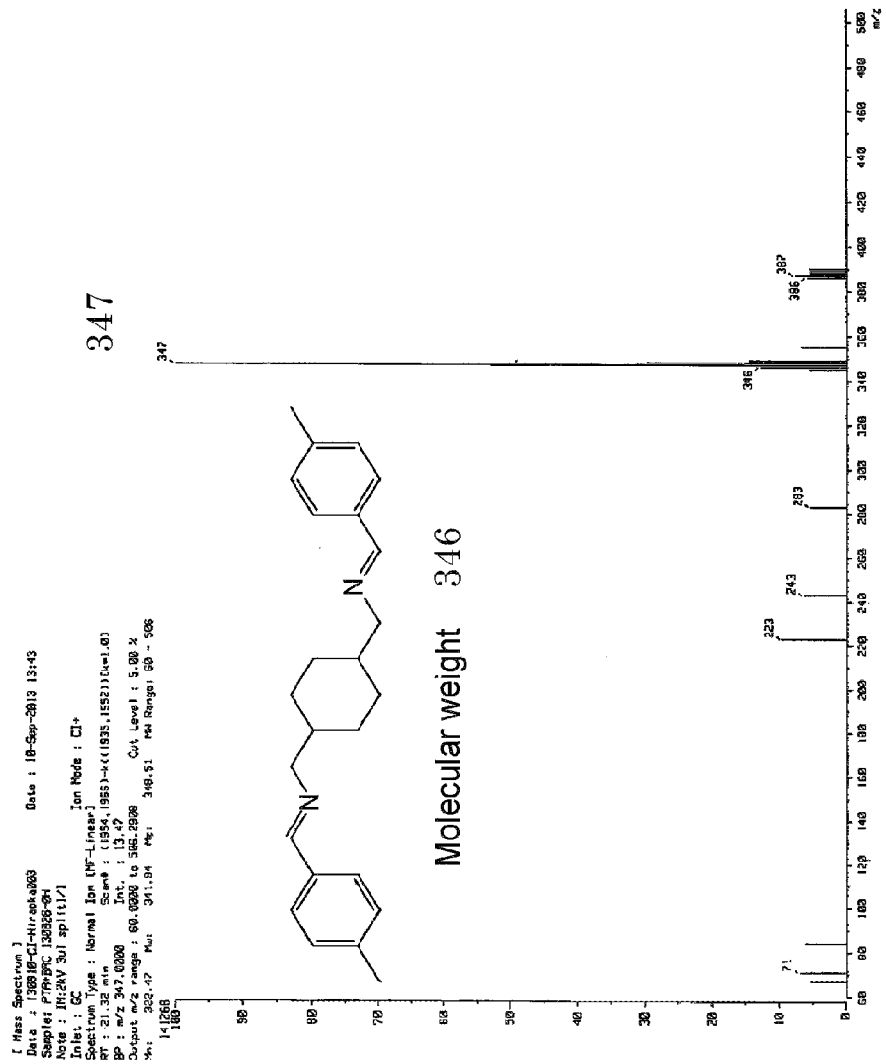
FIG. 6 shows a CI-MS spectrum of peak 4 of the gas chromatograph of Example 4.
Figure 7:
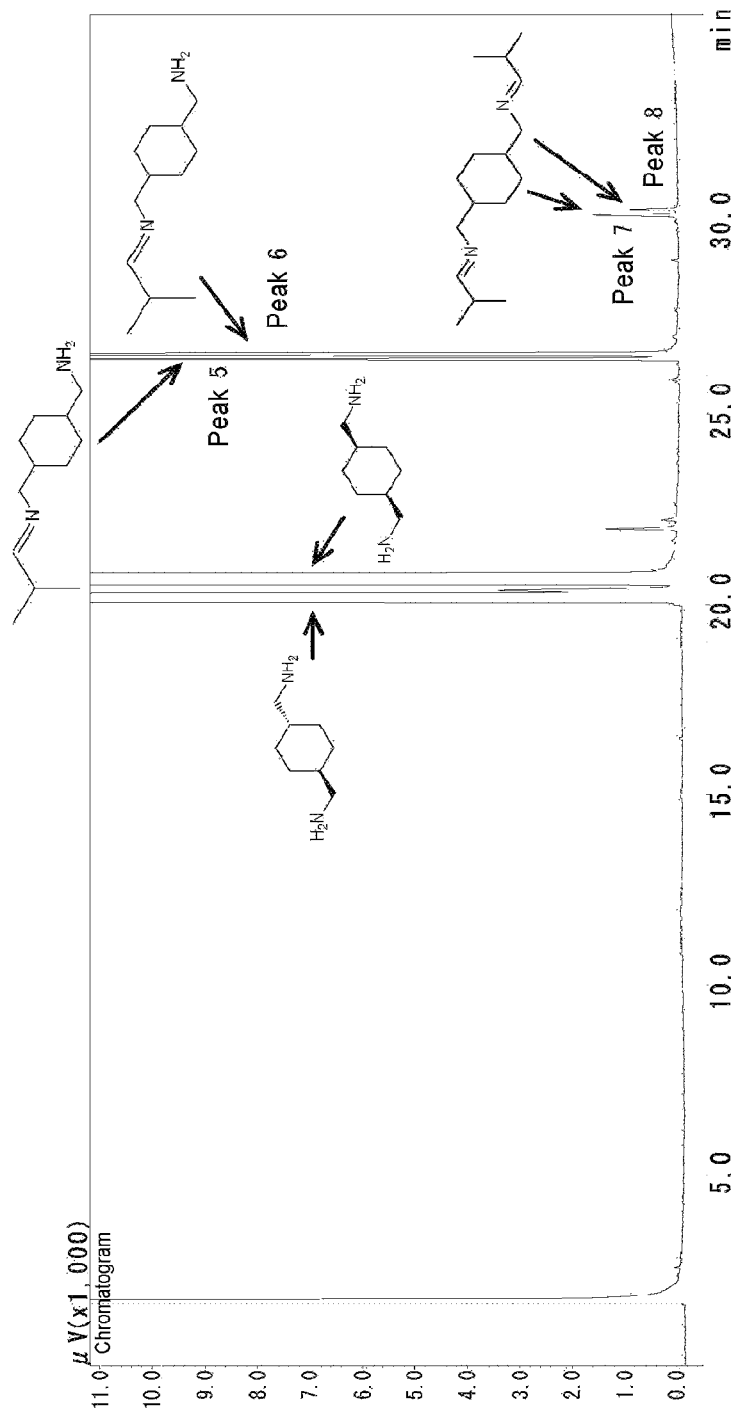
FIG. 7 shows a gas chromatograph of the reaction solution obtained in Example 20.
Figure 8:
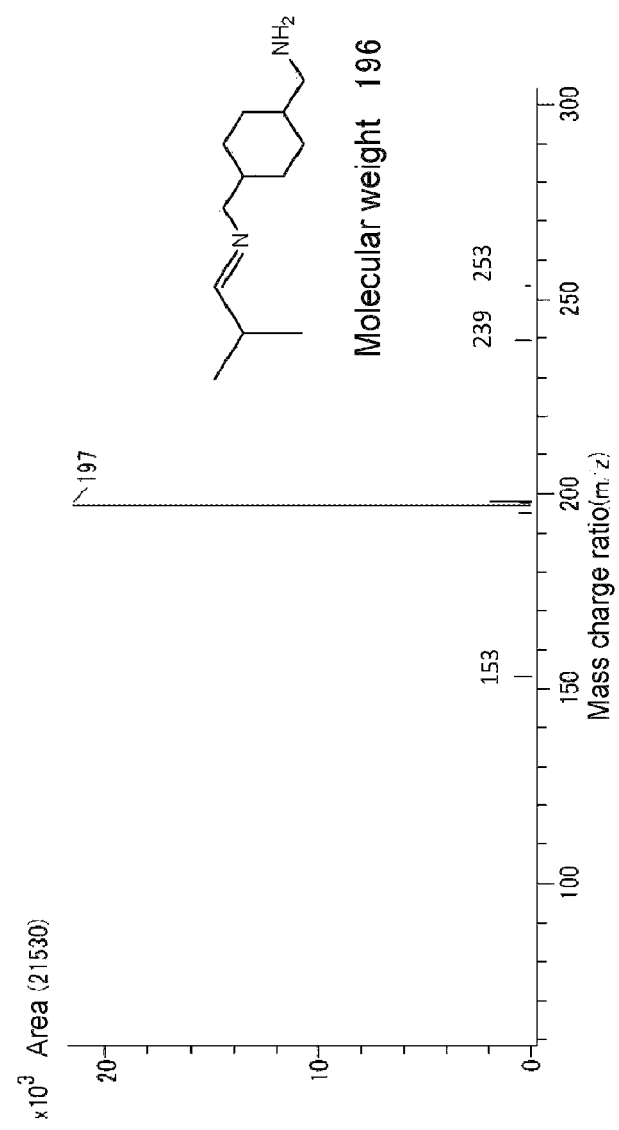
FIG. 8 shows a CI-MS spectrum of peak 5 of the gas chromatograph of Example 20.
Figure 9:
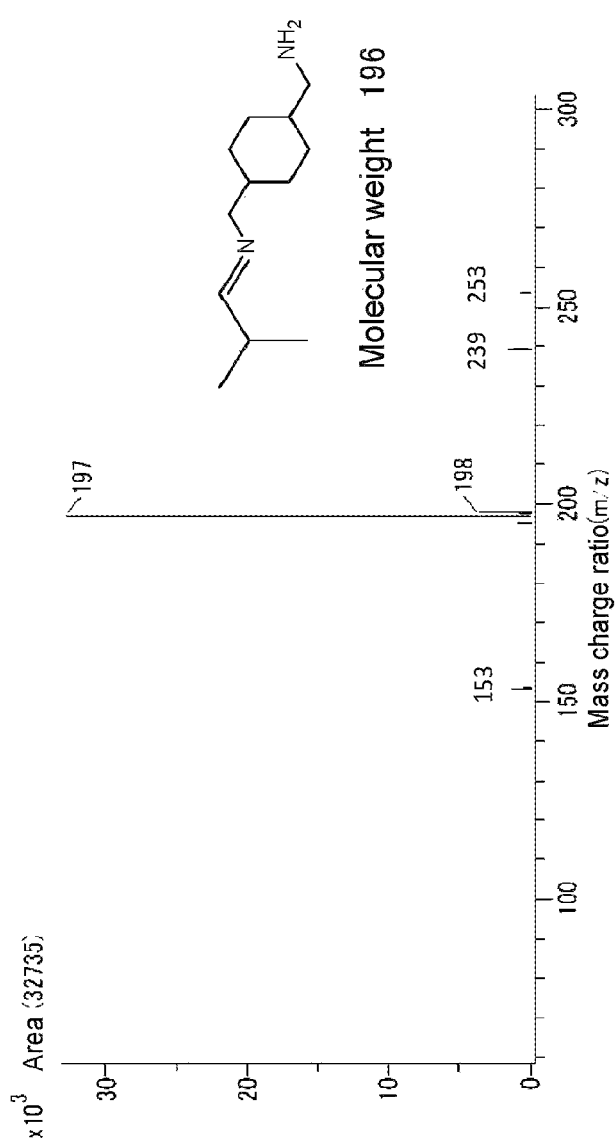
FIG. 9 shows a CI-MS spectrum of peak 6 of the gas chromatograph of Example 20.
Figure 10:
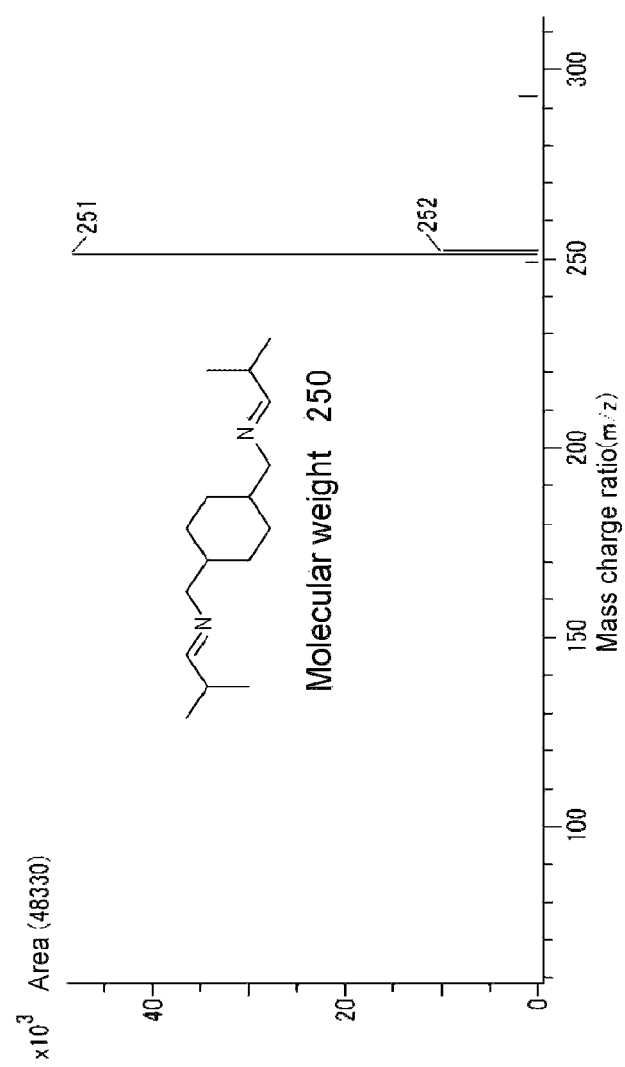
FIG. 10 shows a CI-MS spectrum of peak 7 of the gas chromatograph of Example 20.
Figure 11:
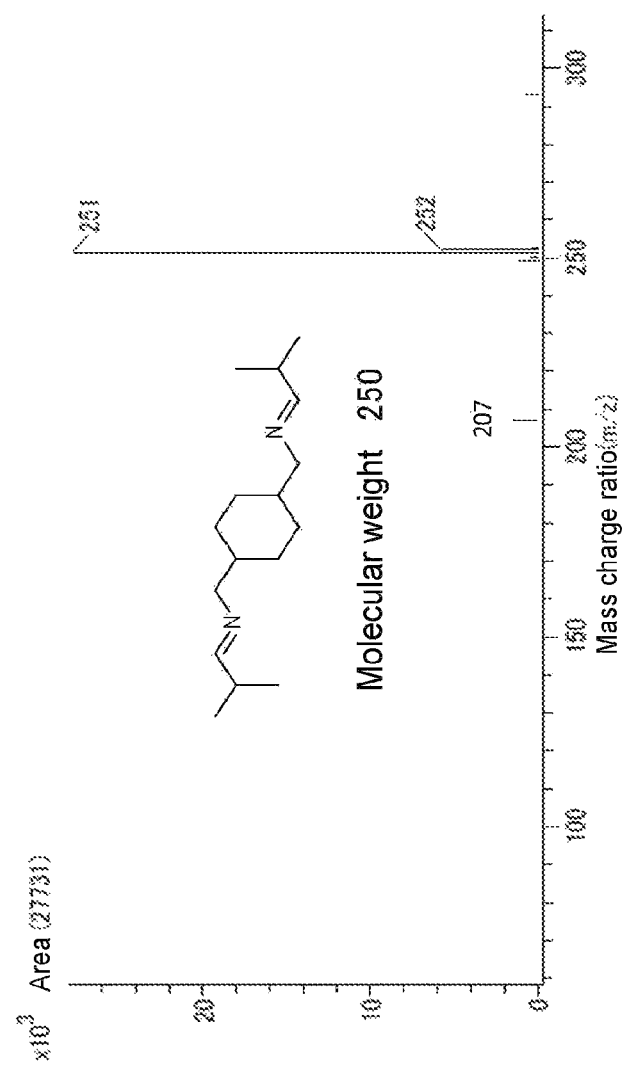
FIG. 11 shows a CI-MS spectrum of peak 8 of the gas chromatograph of Example 20.
Figure 12:
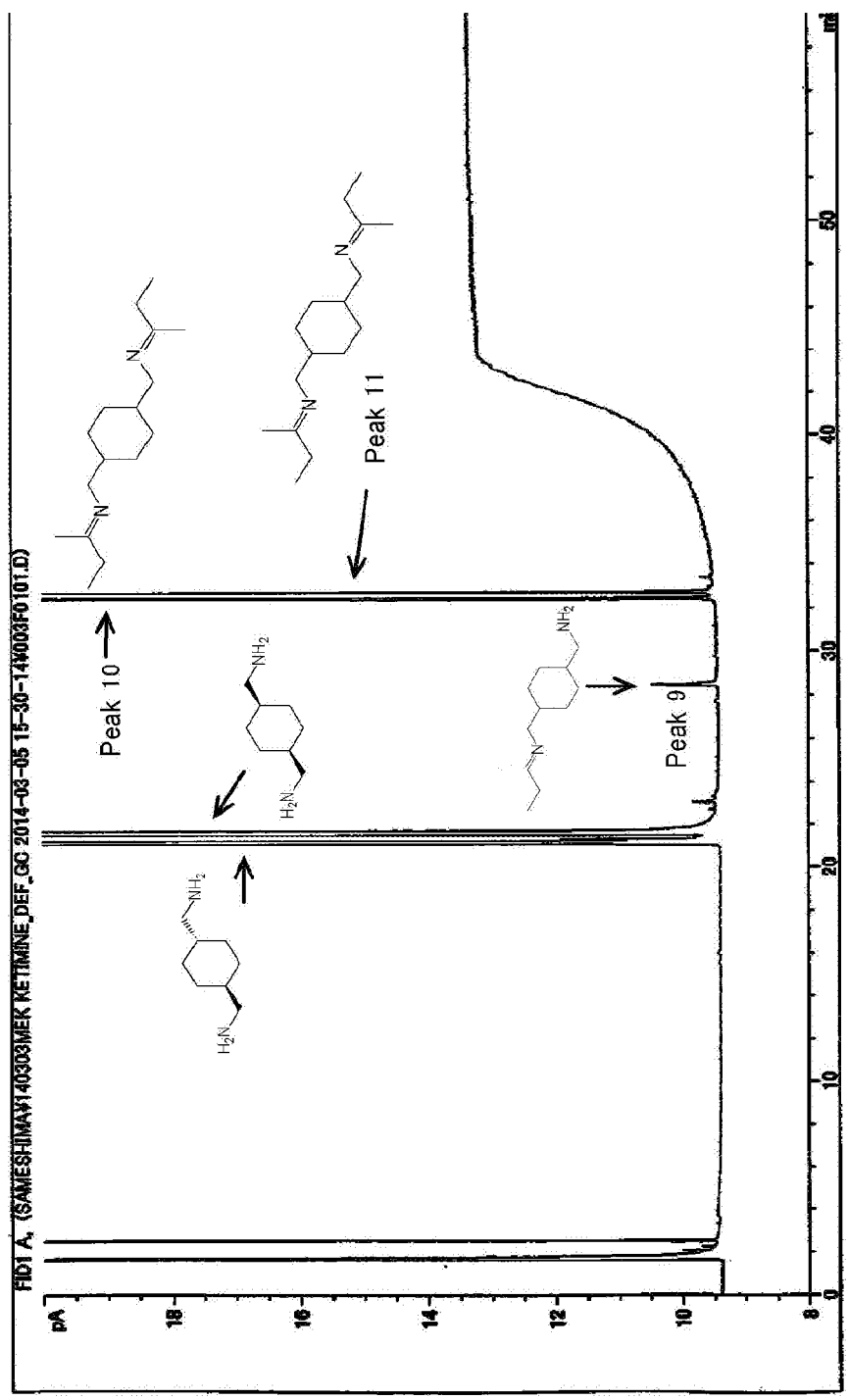
FIG. 12 shows a gas chromatograph of the reaction solution obtained in Example 28.
Figure 13:
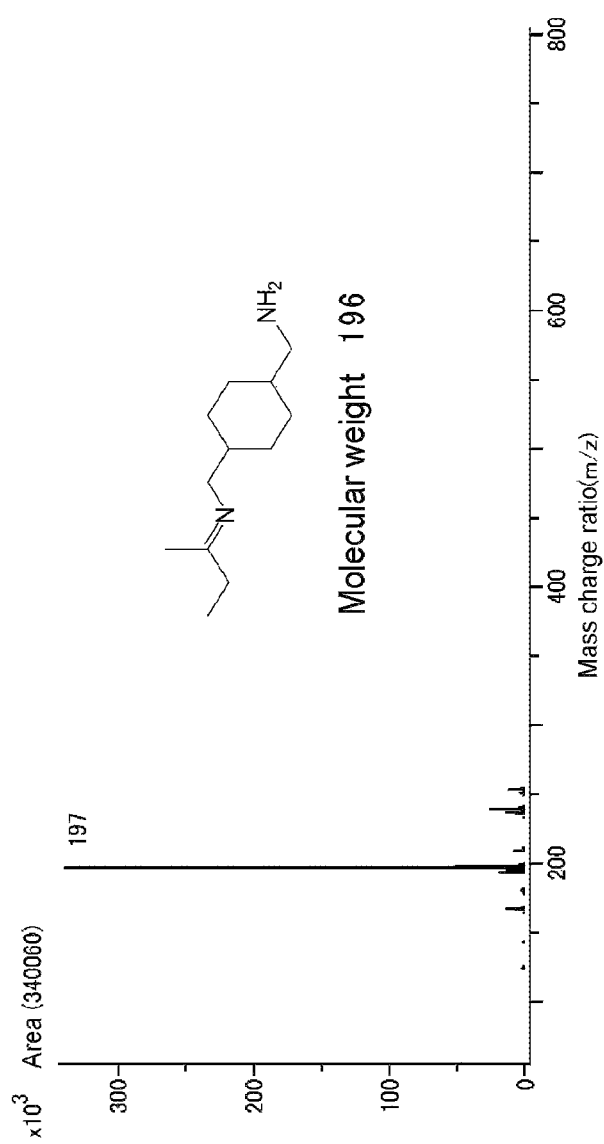
FIG. 13 shows a CI-MS spectrum of peak 9 of the gas chromatograph of Example 28.
Figure 14:
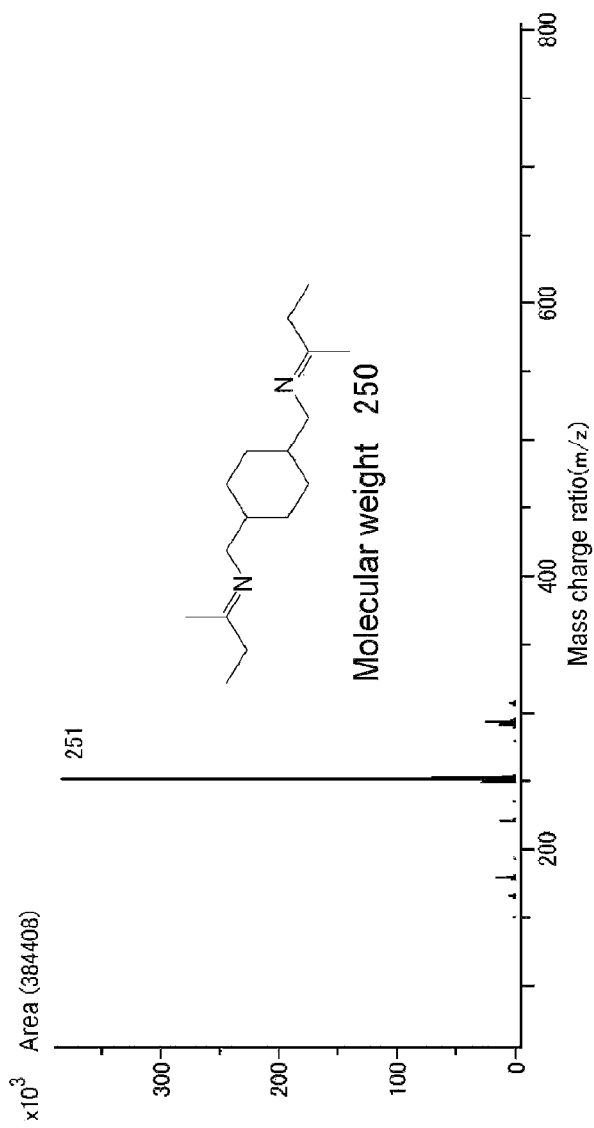
FIG. 14 shows a CI-MS spectrum of peak 10 of the gas chromatograph of Example 28.
Figure 15:
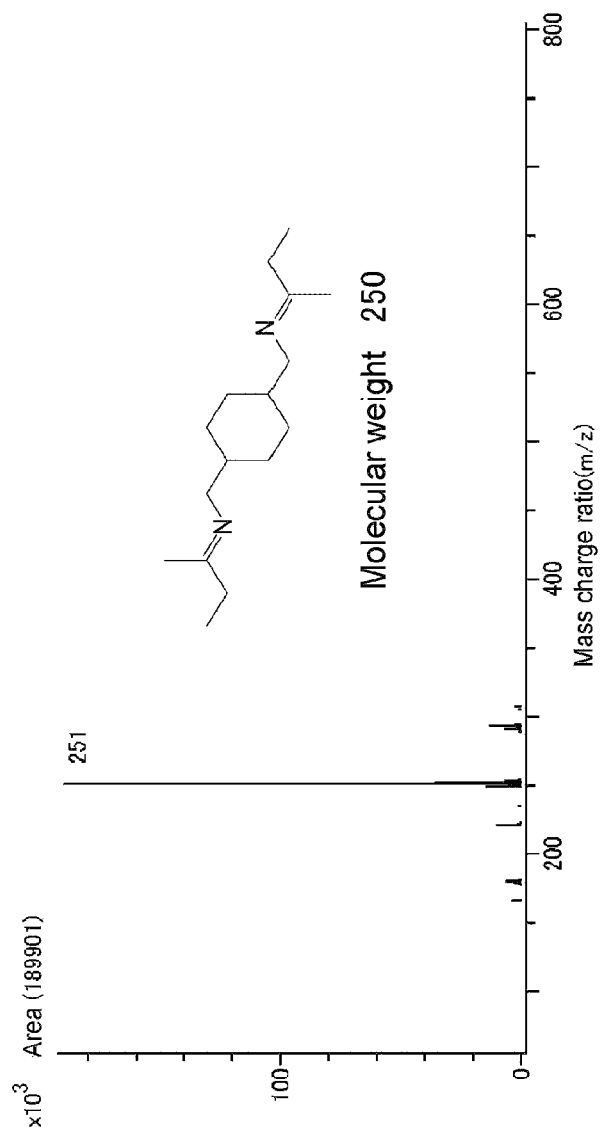
FIG. 15 shows a CI-MS spectrum of peak 11 of the gas chromatograph of Example 28.
Figure 16:
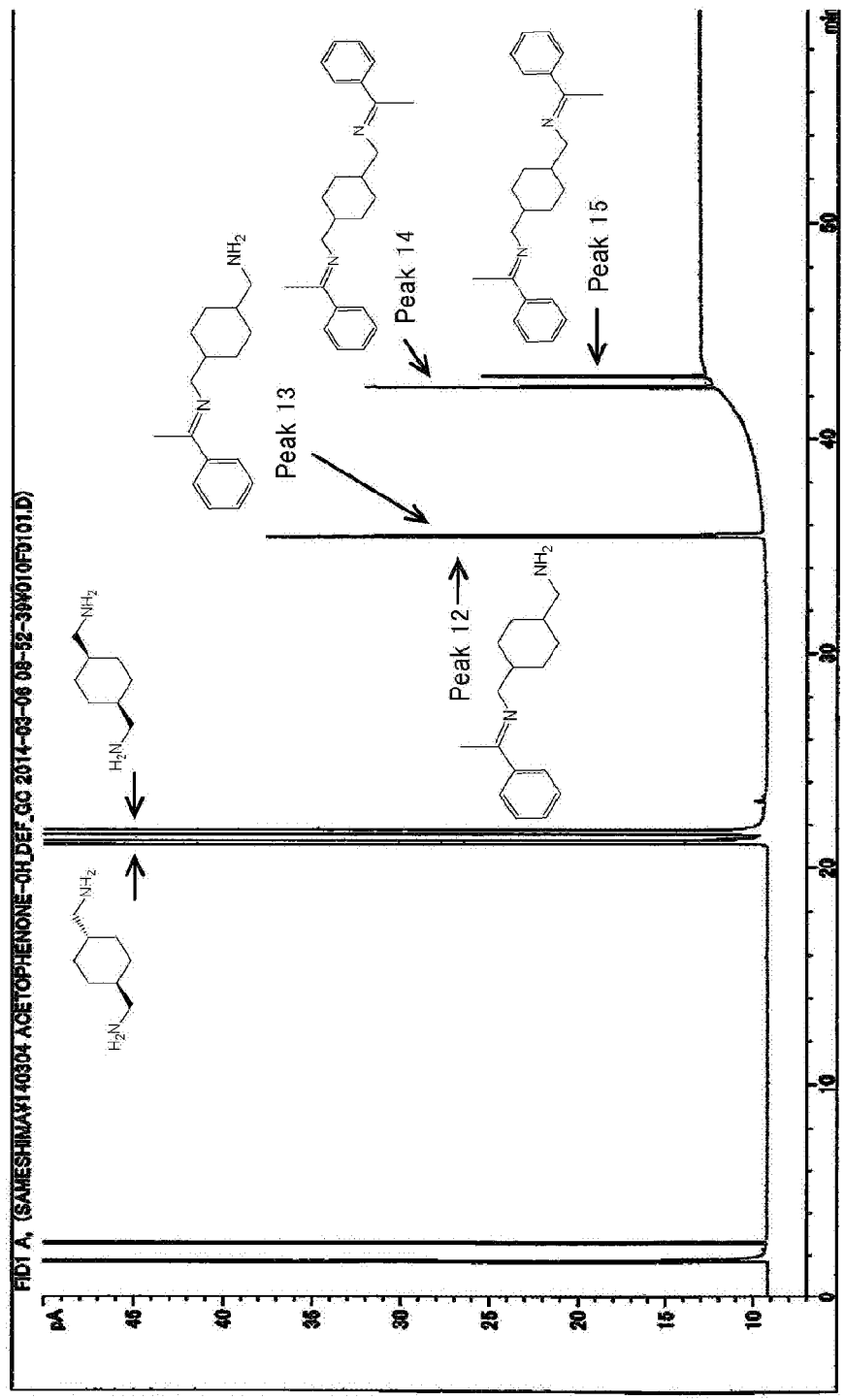
FIG. 16 shows a gas chromatograph of the reaction solution obtained in Example 29.
Figure 17:
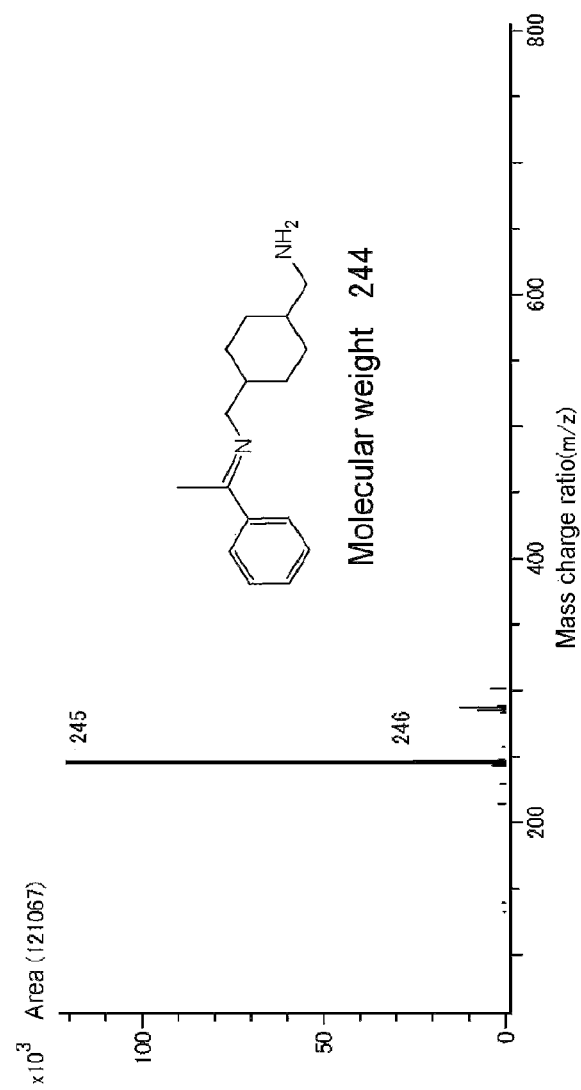
FIG. 17 shows a CI-MS spectrum of peak 12 of the gas chromatograph of Example 29.
Figure 18:
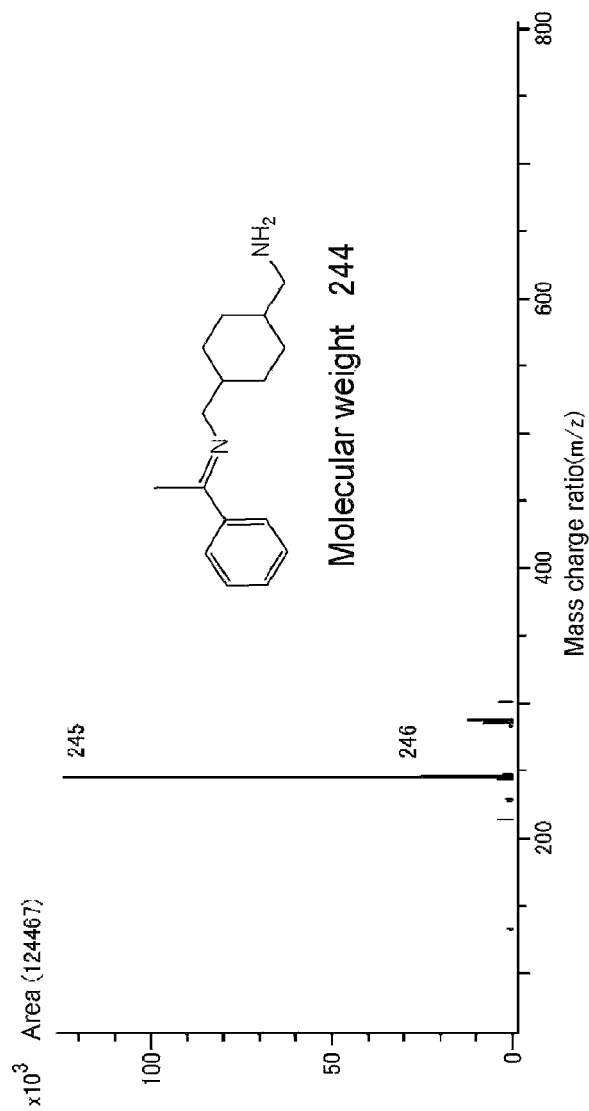
FIG. 18 shows a CI-MS spectrum of peak 13 of the gas chromatograph of Example 29.
Figure 19:
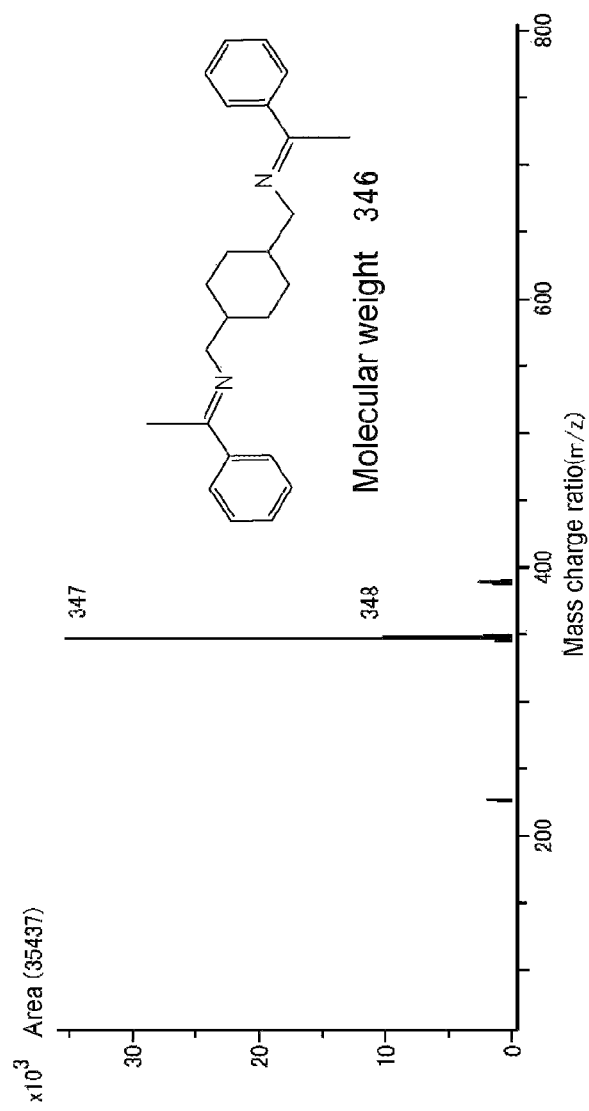
FIG. 19 shows a CI-MS spectrum of peak 14 of the gas chromatograph of Example 29.
Figure 20:
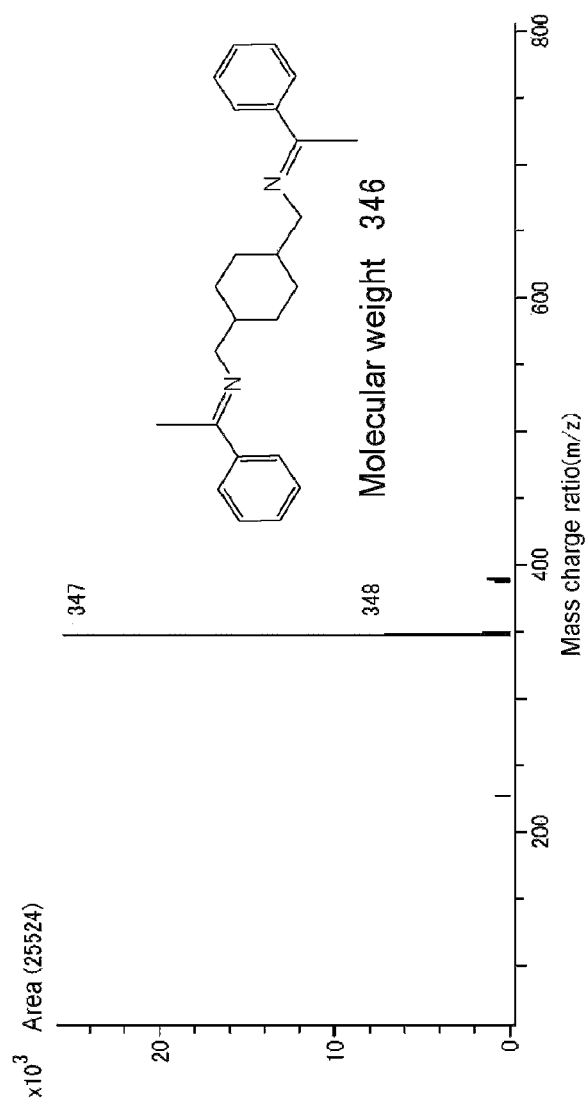
FIG. 20 shows a CI-MS spectrum of peak 15 of the gas chromatograph of Example 29.

Metaxylylenediamine (10 g) was weighed and placed in a flask equipped with a dean stark apparatus and heated to 80° C. Thereafter, benzaldehyde (15.5 g) dissolved in benzene 100 mL was added dropwise to the reaction solution over 30 minutes. After that, benzene was refluxed for one hour to remove water. Benzene was removed by an evaporator. To the resultant residue, hexane (100 mL) was added to perform crystallization. The crystal particles were collected by filtration. The resultant crystal particles were washed with hexane (100 mL) and dried under reduced pressure to obtain a white powder (21.3 g). The CI-MS spectrum (spectrum was observed at a molecular weight+1) of the powder was measured by a time-of-flight mass spectrometer (model JMS-T100GCV) manufactured by JEOL. As a result, peak 1 was detected at a molecular weight of 312. From this, it was confirmed that a compound represented by the following formula (11) was produced (purity: 99%). The gas chromatograph and CI-MS spectrum are shown in FIG. 1 and FIG. 2.

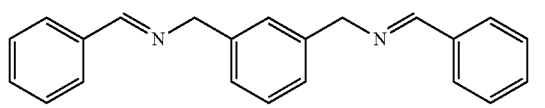

(11)

1,4-Bis(aminomethyl)cyclohexane (cis/trans=60/40) (100 g) and 5.2 g of a compound represented by the following formula (11) and obtained by the aforementioned operation were weighed and placed in a 300 mL-flask, and then sodium amide (2.0 g) was added under an argon gas stream. An isomerization reaction was performed at 120° C. for 4 hours. The isomer composition (cis/trans) after the isomerization reaction was 16/84 and the isomerization yield was 75%.

Example 4

Imine compound: Condensate of 1,4-bis(aminomethyl)cyclohexane and 4-methylbenzaldehyde 1,4-Bis(aminomethyl)cyclohexane (cis/trans=59/41) (100 g) and benzene (100 mL) were weighed and placed in a flask equipped with a dean stark apparatus. To the reaction solution, 2.1 g of 4-methylbenzaldehyde (manufactured by Wako Pure Chemical Industries Ltd.) dissolved in benzene (20 mL) was added dropwise over 30 minutes while refluxing benzene. Thereafter, reflux was continued for one hour to remove water.

The CI-MS spectrum of the reaction solution dewatered was measured by a double focusing mass spectrometer (model JMS-SX102) manufactured by JEOL. As a result, peak 2 (at a molecular weight of 244) and peak 3, peak 4 (at a molecular weight of 346) were detected. From this, it was confirmed that a compound represented by the following formula (12) and a compound represented by the following formula (13) were produced. The gas chromatograph and CI-MS spectra are shown in FIG. 3 to FIG. 6.

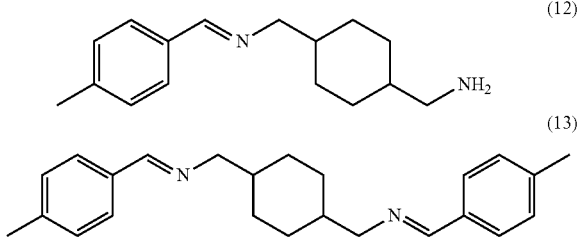

The reaction solution dewatered was distillated to remove benzene. To the solution, sodium amide (2.0 g) was added under an argon gas stream. An isomerization reaction of 1,4-bis(aminomethyl)cyclohexane was carried out at 120° C. for 4 hours. The resultant isomer composition (cis/trans) was 17/83 and the isomerization yield was 91%.

Example 5

Aromatic aldehyde: 4-Methylbenzaldehyde 1,4-Bis(aminomethyl)cyclohexane (cis/trans=59/41) (800 g) and benzene (400 mL) were weighed and placed in a flask equipped with a dean stark apparatus. To the reaction solution, 16 g of 4-methylbenzaldehyde (manufactured by Wako Pure Chemical Industries Ltd.) was added dropwise over 30 minutes while refluxing benzene. Thereafter, reflux was continued for one hour to remove water. After a benzene solvent was removed by distillation, sodium amide (20 g) was added under an argon gas stream. An isomerization reaction was carried out at 120° C. for 4 hours. The resultant isomer composition (cis/trans) was 17/83.

After the isomerization reaction, a single distillation operation was carried out at a bottom temperature of 102° C. and 0.3 kPa. As a result, 1,4-bis(aminomethyl)cyclohexane (700 g) having a purity 99% or more was obtained. The isomer composition (cis/trans) in this case was 16/84 and the isomerization yield was 88%.

Example 6

Aromatic aldehyde: 4-Ethylbenzaldehyde

The isomerization reaction was carried out in the same conditions as in Example 5 except that 4-ethylbenzaldehyde was used in place of 4-methylbenzaldehyde. The resultant isomer composition (cis/trans) was 18/82 and the isomerization yield was 93%.

Example 7

Aromatic aldehyde: 2,4-Dimethylbenzaldehyde

The isomerization reaction was carried out in the same conditions as in Example 5 except that 2,4-dimethylbenzaldehyde was used in place of 4-methylbenzaldehyde. The resultant isomer composition (cis/trans) was 19/81 and the isomerization yield was 930.

Example 8

Aromatic aldehyde: 3,4-Dimethylbenzaldehyde

The isomerization reaction was carried out in the same conditions as in Example 5 except that 3,4-dimethylbenzaldehyde was used in place of 4-methylbenzaldehyde. The resultant isomer composition (cis/trans) was 17/83 and the isomerization yield was 93%.

Example 9

Aromatic aldehyde: 2,4,5-Trimethylbenzaldehyde

The isomerization reaction was carried out in the same conditions as in Example 5 except that 2,4,5-trimethylbenzaldehyde was used in place of 4-methylbenzaldehyde. The resultant isomer composition (cis/trans) was 19/81 and the isomerization yield was 94%.

Example 10

Aromatic aldehyde: 2,4,6-Trimethylbenzaldehyde

The isomerization reaction was carried out in the same conditions as in Example 5 except that 2,4,6-trimethylbenzaldehyde was used in place of 4-methylbenzaldehyde. The resultant isomer composition (cis/trans) was 18/82 and the isomerization yield was 93%.

Example 11

Aromatic aldehyde: 4-Isopropylbenzaldehyde

The isomerization reaction was carried out in the same conditions as in Example 5 except that 4-isopropylbenzaldehyde was used in place of 4-methylbenzaldehyde. The resultant isomer composition (cis/trans) was 17/83 and the isomerization yield was 93%.

Example 12

Aromatic aldehyde: 4-Isobutylbenzaldehyde

The isomerization reaction was carried out in the same conditions as in Example 5 except that 4-isobutylbenzaldehyde was used in place of 4-methylbenzaldehyde. The resultant isomer composition (cis/trans) was 17/83 and the isomerization yield was 92%.

Example 13

Aromatic aldehyde: 4-Biphenylaldehyde

The isomerization reaction was carried out in the same conditions as in Example 5 except that 4-biphenylaldehyde was used in place of 4-methylbenzaldehyde. The resultant isomer composition (cis/trans) was 18/82 and the isomerization yield was 92%.

Example 14

Aromatic aldehyde: 2-Naphthaldehyde

The isomerization reaction was carried out in the same conditions as in Example 5 except that 2-naphthaldehyde was used in place of 4-methylbenzaldehyde. The resultant isomer composition (cis/trans) was 17/83 and the isomerization yield was 91%.

Example 15

Figure 21:
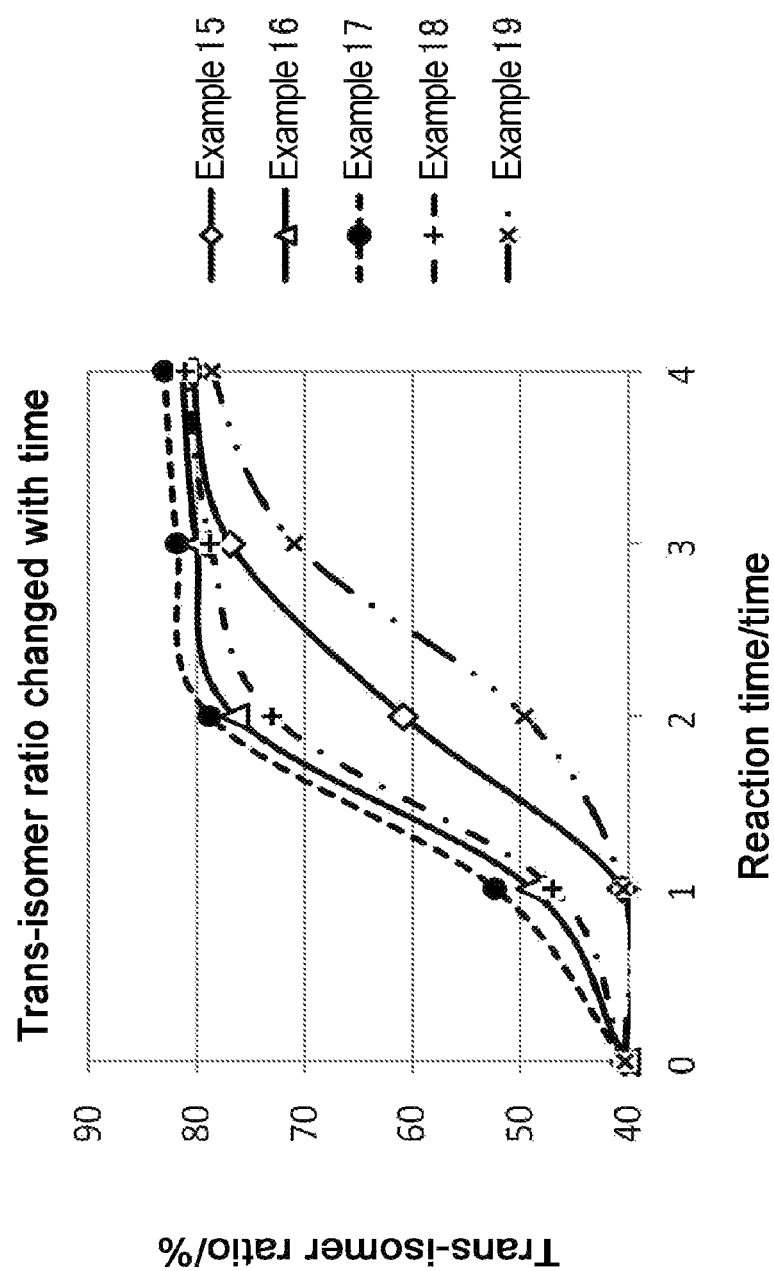
FIG. 21 shows the trans-isomer ratio of each of Examples 15 to 19 changed with time.

1,4-Bis(aminomethyl)cyclohexane (cis/trans=60/40)(400 g) and 4.0 g of 4-methylbenzaldehyde (manufactured by Wako Pure Chemical Industries Ltd.) were weighed and placed in a 1-L flask. The reaction solution was stirred under an argon atmosphere at 120° C. for 30 minutes. Thereafter, the reaction solution was dewatered under reduced pressure at 8 Torr and a temperature of 130° C. for one hour. After that, sodium amide (1.4 g) was added and a pipe made of SUS316 and having a diameter of 3 mmφ was inserted in the reaction solution. While blowing argon gas into the solution through the pipe at a flow rate of 80 mL/min, isomerization was performed at 120° C. for 4 hours. The isomer composition (cis/trans) two hours after initiation of the isomerization reaction was 39/61. The isomer composition (cis/trans) four hours after initiation of the isomerization reaction was 20/80. A change in trans-isomer ratio with the passage of time is shown in FIG. 21.

Example 16

The isomerization reaction was carried out in the same conditions as in Example 15 except that the argon flow rate was changed to 200 mL/min. The isomer composition (cis/trans) two hours after initiation of the isomerization reaction was 23/76. The isomer composition (cis/trans) four hours after initiation of the isomerization reaction was 19/81. The isomerization yield after the reaction was 92%. A change in trans-isomer ratio with the passage of time is shown in FIG. 21.

Example 17

The isomerization reaction was carried out in the same conditions as in Example 15 except that the argon flow rate was changed to 500 mL/min. The isomer composition (cis/trans) two hours after initiation of the isomerization reaction was 21/79. The isomer composition (cis/trans) four hours after initiation of the isomerization reaction was 17/83. The isomerization yield after the reaction was 92%. A change in trans-isomer ratio with the passage of time is shown in FIG. 21.

Example 18

1,4-Bis(aminomethyl)cyclohexane (cis/trans=60/40) (400 g) and 4.0 g of 4-methylbenzaldehyde (manufactured by Wako Pure Chemical Industries Ltd.) were weighed and placed in a 1-L flask. The reaction solution was stirred under an argon atmosphere at 120° C. for 30 minutes. Thereafter, the reaction solution was dewatered under reduced pressure at 8 Torr and a temperature of 130° C. for one hour. After that, benzene (80 g) and sodium amide (1.4 g) were added under an argon atmosphere and isomerization was carried out at 120° C. for 4 hours. The isomer composition (cis/trans) two hours after initiation of the isomerization reaction was 27/73. The isomer composition (cis/trans) four hours after initiation of the isomerization reaction was 19/81. The isomerization yield after the reaction was 94%. A change in trans-isomer ratio with the passage of time is shown in FIG. 21.

Example 19

The isomerization reaction was carried out in the same conditions as in Example 18 except that sodium amide (1.4 g) was added under an argon atmosphere after water was removed and benzene was not added. The isomer composition (cis/trans) two hours after initiation of the isomerization reaction was 50/50. The isomer composition (cis/trans) four hours after initiation of the isomerization reaction was 21/79. A change in trans-isomer ratio with the passage of time is shown in FIG. 21.

Example 20

Imine compound: Condensate of 1,4-bis(aminomethyl)cyclohexane and isobutyraldehyde 1,4-Bis(aminomethyl)cyclohexane (cis/trans=60/40)(200 g) and 2.5 g of isobutyraldehyde (purity: 97% or more, manufactured by Wako Pure Chemical Industries Ltd.) were weighed and placed in a 500-mL flask. The reaction solution was stirred under an argon atmosphere at 120° C. for 30 minutes. Thereafter, the reaction solution was dewatered under reduced pressure at 8 Torr and a temperature of 130° C. for 1.5 hours.

The CI-MS spectrum of the reaction solution dewatered was measured by a time-of-flight mass spectrometer (model JMS-T100GCV) manufactured by JEOL. As a result, peaks 5 and 6 at a molecular weight of 196 and peaks 7 and 8 at a molecular weight of 250 were detected. From this, it was confirmed that a compound represented by the following formula (14) and a compound represented by the following formula (15) are produced. The gas chromatograph and CI-MS spectra is shown in FIG. 7 to FIG. 11.

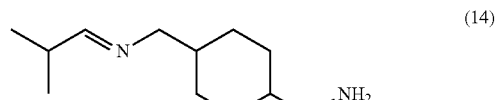

(14)

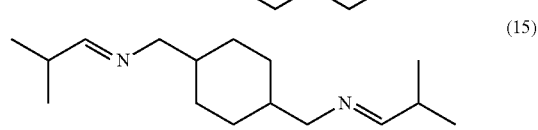

(15)

To the reaction solution dewatered, sodium amide (4.0 g) was added under an argon gas stream and an isomerization reaction was carried out at 120° C. for 4 hours. The resultant isomer composition (cis/trans) was 17/83 and the isomerization yield was 90%.

Example 21

Aliphatic Aldehyde: Isobutyraldehyde 1,4-Bis(aminomethyl)cyclohexane (cis/trans=60/40)(400 g) and 2.5 g of isobutyraldehyde (purity: 97% or more, manufactured by Wako Pure Chemical Industries Ltd.) were weighed and placed in a 1-L flask. The reaction solution was stirred at 120° C. for 30 minutes. Thereafter, the reaction solution was dewatered under reduced pressure at 8 Torr and a temperature of 130° C. for 1.5 hours. After that, sodium amide (1.5 g) was added under an argon gas stream and an isomerization reaction was carried out at 120° C. for 4 hours. The resultant isomer composition (cis/trans) was 18/82.

The isomerization reaction solution was subjected to a single distillation operation at a bottom temperature of 110° C. and 0.4 kPa. As a result, 1,4-bis(aminomethyl)cyclohexane (368 g) having a purity 95% or more was obtained (isomerization yield of 92%). The isomer composition (cis/trans) in this case was 16/84.

Example 22

Aliphatic Aldehyde: Acetaldehyde

The isomerization reaction was carried out in the same manner as in Example 20 except that 1.7 g of acetaldehyde (an aqueous 90% acetaldehyde solution manufactured by Wako Pure Chemical Industries Ltd.) was used in place of isobutyraldehyde. The resultant isomer composition (cis/trans) was 19/81 and the isomerization yield was 92%.

Example 23

Aliphatic aldehyde: n-Decylaldehyde

The isomerization reaction was carried out in the same manner as in Example 20 except that 5.5 g of n-decylaldehyde (purity: 95% or more, manufactured by Tokyo Chemical Industry Co., Ltd.) was used in place of isobutyraldehyde. The resultant isomer composition (cis/trans) was 16/84 and the isomerization yield was 90%.

Example 24

Aliphatic Aldehyde: Methacrolein

The isomerization reaction was carried out in the same manner as in Example 20 except that 3.0 g of methacrolein (purity: 80% or more, manufactured by Tokyo Chemical Industry Co., Ltd.) was used in place of isobutyraldehyde. The resultant isomer composition (cis/trans) was 18/82 and the isomerization yield was 88%.

Example 25

Aliphatic Aldehyde: Formaldehyde

The isomerization reaction was carried out in the same conditions as in Example 20 except that 2.8 g of formaldehyde (36 to a 38% aqueous formaldehyde solution, manufactured by Wako Pure Chemical Industries Ltd.) was used in place of isobutyraldehyde. The resultant isomer composition (cis/trans) was 25/75 and the isomerization yield was 90%.

Example 26

Aliphatic Aldehyde: Glyoxal

The isomerization reaction was carried out in the same conditions as in Example 20 except that 4.9 g of glyoxal (39% aqueous solution, manufactured by Tokyo Chemical Industry Co., Ltd.) was used in place of isobutyraldehyde. The resultant isomer composition (cis/trans) was 24/76 and the isomerization yield was 88%.

Example 27

Aliphatic Aldehyde: Cinnamaldehyde

The isomerization reaction was carried out in the same conditions as in Example 20 except that 4.4 g of cinnamaldehyde (purity: 98% or more, manufactured by Wako Pure Chemical Industries Ltd.) was used in place of isobutyraldehyde and the addition amount of sodium amide was changed to 1.5 g. The resultant isomer composition (cis/trans) was 21/79 and the isomerization yield was 92%.

Example 28

Ketone: Methyl Ethyl Ketone 1,4-Bis(aminomethyl)cyclohexane (cis/trans=60/40)(100 g), 1.2 g of methyl ethyl ketone (purity: 99% or more, manufactured by Tokyo Chemical Industry Co., Ltd.) and benzene (100 mL) were weighed and placed in a 500 mL flask equipped with a dean stark apparatus. The reaction solution was subjected to an azeotropic dehydration treatment for 4 hours while refluxing benzene.

The CI-MS spectrum of the reaction solution dewatered was measured by a time-of-flight mass spectrometer (model JMS-T100GCV) manufactured by JEOL. As a result, peak 9 at a molecular weight of 196 and peaks 10 and 11 at a molecular weight of 250 were detected. From this, it was confirmed that a compound represented by the following formula (16) and a compound represented by the following formula (17) are produced. The as chromatograph and CI-MS spectra are shown in FIG. 12 to FIG. 15.

After benzene was removed from the reaction solution dewatered, sodium amide (2.0 g) was added under an argon gas stream. An isomerization reaction was carried out at 120° C. for 4 hours. The resultant isomer composition (cis/trans) was 16/84 and the isomerization yield was 89%.

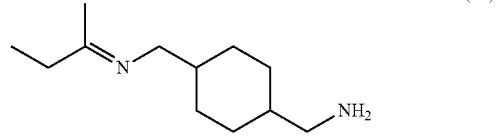

(16)

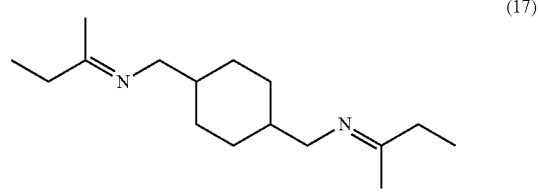

(17)

Example 29

Ketone: Acetophenone 1,4-Bis(aminomethyl)cyclohexane (cis/trans=60/40)(100 g) and 2.0 g of acetophenone (purity: 98.5% or more, manufactured by Tokyo Chemical Industry Co., Ltd.) were weighed and placed in a 300 mL flask. To this, 5 g of activated alumina (GP-20, manufactured by MIZUSAWA INDUSTRIAL CHEMICALS, Ltd.) was added as an acid catalyst. The reaction solution was stirred under an argon atmosphere at a temperature of 160° C. for 3 hours.

The CI-MS spectrum of the reaction solution stirred was measured by a time-of-flight mass spectrometer (model JMS-T100GCV) manufactured by JEOL. As a result, peaks 12 and 13 at a molecular weight of 244 and peaks 14 and 15 at a molecular weight of 346 were detected. From this, it was confirmed that a compound represented by the following formula (18) and a compound represented by the following formula (19) are produced. The gas chromatograph and CI-MS spectra are shown in FIG. 16 to FIG. 20.

From the reaction solution stirred, alumina was removed by a filtration operation. The filtrate was recovered and dewatered under reduced pressure at 8 Torr and a temperature of 130° C. for 1.5 hours. After that, sodium amide (1.9 g) was added under an argon gas stream and an isomerization reaction was carried out at 120° C. for 4 hours. The resultant isomer composition (cis/trans) was 18/82 and the isomerization yield was 81%.

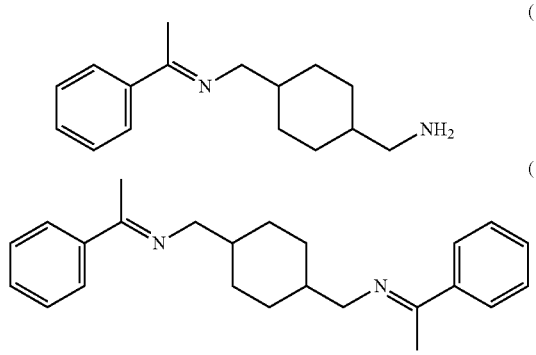

(18)

(19)

Example 30

Alkali Species: Sodium Hydride

The isomerization reaction was carried out in the same conditions as in Example 4 except that sodium hydride (in oil, content: 50 to 70%, manufactured by Wako Pure Chemical Industries Ltd.) was used in place of sodium amide. The resultant isomer composition (cis/trans) was 23/77 and the isomerization yield was 93%.

Example 31

Alkali Species: Sodium

The isomerization reaction was carried out in the same conditions as in Example 4 except that metallic sodium (Sodium 30 to 35 wt % dispersion in paraffin wax, manufactured by Sigma-Aldrich) was used in place of sodium amide. The resultant isomer composition (cis/trans) was 21/79 and the isomerization yield was 95%.

Example 32

Alkali Species: Lithium Amide 1,4-Bis(aminomethyl)cyclohexane (cis/trans=60/40)(100 g) and 2.0 g of 4-methylbenzaldehyde (manufactured by Wako Pure Chemical Industries Ltd.) were weighed and placed in a 300 mL flask. The reaction solution was stirred at 120° C. for 30 minutes under an argon atmosphere. Thereafter, the reaction solution was dewatered under reduced pressure at 8 Torr and a temperature of 130° C. for 2 hours. After that, lithium amide (1.1 g) was added under an argon gas stream. An isomerization reaction was carried out at 120° C. for 4 hours. The resultant isomer composition (cis/trans) was 18/82, and the isomerization yield was 88%.

Example 33

Bis(aminomethyl)cyclohexane: 1,3-Bis(aminomethyl)cyclohexane 1,3-Bis(aminomethyl)cyclohexane (cis/trans=74/26)(100 g) and benzene (100 mL) were weighed and placed in a flask equipped with a dean stark apparatus. To the flask, 2 g of 4-methylbenzaldehyde dissolved in benzene (20 mL) was added dropwise over 30 minutes while refluxing benzene. After that, reflux was continued for one hour to remove water. After the benzene solvent was removed by distillation, sodium amide (2 g) was added under an argon gas stream. An isomerization reaction was carried out at 120° C. for 4 hours. The resultant isomer composition (cis/trans) was 80/20 and the isomerization yield was 94%.

Example 34

Aromatic aldehyde: 2,4,5-Trimethylbenzaldehyde

The isomerization reaction was carried out in the same conditions as in Example 33 except that 2,4,5-trimethylbenzaldehyde was used in place of 4-methylbenzaldehyde. The resultant isomer composition (cis/trans) was 80/20 and the isomerization yield was 93%.

Comparative Example 1

To 100 g of 1,4-bis(aminomethyl)cyclohexane (cis/trans=60/40), 1.9 g of sodium amide was added. The reaction solution was stirred under an argon gas stream at 120° C. for 4 hours. The isomer composition (cis/trans) after a reaction was 47/53 and the isomerization yield was 100%.

Comparative Example 2

To 100 g of 1,4-bis(aminomethyl)cyclohexane (cis/trans=59/41), 4-methylbenzyl amine (2 g) and sodium amide (1 g) were added. The isomerization reaction was carried out under an argon gas atmosphere at 120° C. for 4 hours. The resultant isomer composition (cis/trans) was 30/70.

Comparative Example 3

To 100 g of 1,4-bis(aminomethyl)cyclohexane (cis/trans=59/41), 4-methylbenzyl amine (4 g) and sodium amide (4 g) were added. The isomerization reaction was carried out under an argon atmosphere at 120° C. for 4 hours. The resultant isomer composition (cis/trans) was 23/77.

Change of isomer ratio every time point in Examples and Comparative Examples are shown in Table 1.

TABLE 1

| | | | Example | | | | | | | | | |
|---|---|---|---|---|---|---|---|---|---|---|---|---|
| | | Unit | 1 | 2 | 3 | 4 | 5 | 6 | 7 | 8 | 9 | 10 |
| Starting materials | 1,4-BAC | g | 100 | 100 | 100 | 100 | 800 | 100 | 100 | 100 | 100 | 100 |
| | | mol | 0.70 | 0.70 | 0.70 | 0.70 | 5.60 | 0.70 | 0.70 | 0.70 | 0.70 | 0.70 |
| | Imine compound | g | 3.1 | 2.7 | 5.2 | | | | | | | |
| | | mol | 0.017 | 0.017 | 0.017 | | | | | | | |
| | Aldehyde | g | | | | 2.1 | 16 | 2.3 | 2.3 | 2.3 | 2.5 | 2.5 |
| | | mol | | | | 0.017 | 0.13 | 0.017 | 0.017 | 0.017 | 0.017 | 0.017 |
| | NaNH$_2$ | g | 2.0 | 2.0 | 2.0 | 2.0 | 2.0 | 2.0 | 2.0 | 2.0 | 2.0 | 2.0 |
| | | mol | 0.050 | 0.050 | 0.050 | 0.050 | 0.500 | 0.050 | 0.050 | 0.050 | 0.050 | 0.050 |

TABLE 1-continued

|  |  |  |  |  |  |  |  |  |  |  |  |
|---|---|---|---|---|---|---|---|---|---|---|---|
| Temperature | ° C. |  |  |  |  | 120 |  |  |  |  |  |
| Stirring rate | rpm |  |  |  |  | 200 |  |  |  |  |  |
| Reaction time | hours |  |  |  |  | 4 |  |  |  |  |  |
| Argon gas flow rate for bubbling | mL/min | — | — | — | — | — | — | — | — | — | — |
| Isomer composition (trans-isomer ratio %) changed with time | 0 hours | 40 | 40 | 40 | 41 | 40 | 40 | 40 | 40 | 40 | 40 |
|  | 1 hours | 72 | 75 | 81 | 71 | — | 69 | — | 54 | 72 | — |
|  | 2 hours | 77 | 78 | 83 | 79 | — | 80 | — | 80 | 79 | — |
|  | 3 hours | 80 | 80 | 83 | 81 | — | 81 | — | — | 80 | — |
|  | 4 hours | 81 | 82 | 84 | 83 | 83 | 82 | 81 | 83 | 81 | 82 |
| Isomer composition (cis/trans) |  | 19/81 | 18/82 | 16/84 | 17/83 | 17/83 | 18/82 | 19/81 | 17/83 | 19/81 | 18/82 |
| Isomerization yield | % | 85 | 86 | 75 | 91 | 88 | 93 | 93 | 93 | 94 | 93 |

|  |  |  | Example |  |  |  |  |  |  |  |  |
|---|---|---|---|---|---|---|---|---|---|---|---|
|  |  | Unit | 11 | 12 | 13 | 14 | 15 | 16 | 17 | 18 | 19 |
| Starting materials | 1,4-BAC | g | 100 | 100 | 100 | 100 | 400 | 400 | 400 | 400 | 400 |
|  |  | mol | 0.70 | 0.70 | 0.70 | 0.70 | 2.81 | 2.81 | 2.81 | 2.81 | 2.81 |
|  | Imine compound | g |  |  |  |  |  |  |  |  |  |
|  |  | mol |  |  |  |  |  |  |  |  |  |
|  | Aldehyde | g | 2.5 | 2.7 | 3.0 | 2.6 | 4.0 | 4.0 | 4.0 | 4.0 | 4.0 |
|  |  | mol | 0.017 | 0.017 | 0.017 | 0.017 | 0.033 | 0.033 | 0.033 | 0.033 | 0.033 |
|  | NaNH$_2$ | g | 2.0 | 2.0 | 2.0 | 2.0 | 1.4 | 1.4 | 1.4 | 1.4 | 1.4 |
|  |  | mol | 0.050 | 0.050 | 0.050 | 0.050 | 0.036 | 0.036 | 0.036 | 0.036 | 0.036 |
| Temperature |  | ° C. |  |  |  |  | 120 |  |  |  |  |
| Stirring rate |  | rpm |  |  |  |  | 200 |  |  |  |  |
| Reaction time |  | hours |  |  |  |  | 4 |  |  |  |  |
| Argon gas flow rate for bubbling |  | mL/min | — | — | — | — | 80 | 200 | 500 | 0 | 0 |
| Isomer composition (trans-isomer ratio %) changed with time | 0 hours |  | 40 | 40 | 40 | 40 | 40 | 40 | 40 | 40 | 40 |
|  | 1 hours |  | 75 | — | 60 | 55 | 41 | 49 | 52 | 47 | 40 |
|  | 2 hours |  | 81 | — | 77 | 76 | 61 | 76 | 79 | 73 | 50 |
|  | 3 hours |  | 82 | — | 80 | 82 | 77 | 80 | 82 | 79 | 71 |
|  | 4 hours |  | 83 | 83 | 82 | 83 | 80 | 81 | 83 | 81 | 79 |
| Isomer composition (cis/trans) |  |  | 17/83 | 17/83 | 18/82 | 17/83 | 20/80 | 19/81 | 17/83 | 19/81 | 21/79 |
| Isomerization yield |  | % | 93 | 92 | 92 | 91 | — | 92 | 92 | 94 | — |

1,4-BAC: 1,4-bis(aminomethyl)cyclohexane

TABLE 2

|  |  |  | Example |  |  |  |  |  |  |  |  |
|---|---|---|---|---|---|---|---|---|---|---|---|
|  |  | Unit | 20 | 21 | 22 | 23 | 24 | 25 | 26 | 27 | 28 |
| Starting materials | 1,4-BAC | g | 200 | 400 | 200 | 200 | 200 | 200 | 200 | 200 | 100 |
|  |  | mol | 1.41 | 2.82 | 1.41 | 1.41 | 1.41 | 1.41 | 1.41 | 1.41 | 0.70 |
|  | 1,3-BAC | g |  |  |  |  |  |  |  |  |  |
|  |  | mol |  |  |  |  |  |  |  |  |  |
|  | Aldehyde | g | 2.5 | 2.5 | 1.7 | 5.5 | 3.0 | 2.8 | 4.9 | 4.4 |  |
|  |  | mol | 0.034 | 0.034 | 0.034 | 0.034 | 0.034 | 0.034 | 0.033 | 0.033 |  |
|  | Ketone | g |  |  |  |  |  |  |  |  | 1.2 |
|  |  | mol |  |  |  |  |  |  |  |  | 0.017 |
|  | Amine | g |  |  |  |  |  |  |  |  |  |
|  |  | mol |  |  |  |  |  |  |  |  |  |
|  | NaNH$_2$ | g | 4.0 | 1.5 | 4.0 | 4.0 | 4.0 | 4.0 | 4.0 | 1.5 | 2.0 |
|  |  | mol | 0.10 | 0.038 | 0.10 | 0.10 | 0.10 | 0.10 | 0.10 | 0.038 | 0.050 |
|  | NaH | g |  |  |  |  |  |  |  |  |  |
|  |  | mol |  |  |  |  |  |  |  |  |  |
|  | Na | g |  |  |  |  |  |  |  |  |  |
|  |  | mol |  |  |  |  |  |  |  |  |  |
|  | LiNH$_2$ | g |  |  |  |  |  |  |  |  |  |
|  |  | mol |  |  |  |  |  |  |  |  |  |
| Temperature |  | ° C. |  |  |  |  | 120 |  |  |  |  |
| Stirring rate |  | rpm |  |  |  |  | 200 |  |  |  |  |
| Reaction time |  | hours |  |  |  |  | 4 |  |  |  |  |
| Isomer composition (trans-isomer ratio %) changed with time | 0 hours | 40 | 40 | 40 | 40 | 40 | 40 | 40 | 40 | 40 |
|  | 1 hours | 78 | — | — | 78 | 66 | — | — | — | 67 |
|  | 2 hours | 80 | — | — | 82 | 80 | 69 | — | — | 82 |
|  | 3 hours | 82 | — | — | 83 | 81 | 72 | — | — | 84 |
|  | 4 hours | 83 | 84 | 81 | 84 | 82 | 75 | 76 | 79 | 84 |

TABLE 2-continued

| | | | | | | | | | | | |
|---|---|---|---|---|---|---|---|---|---|---|---|
| Isomer composition (cis/trans) | | | 17/83 | 16/84 | 19/81 | 16/84 | 18/82 | 25/75 | 24/76 | 21/79 | 16/84 |
| Isomerization yield | | % | 90 | 92 | 92 | 90 | 88 | 90 | 88 | 92 | 89 |

| | | | Example | | | | | | Comparative Example | | |
|---|---|---|---|---|---|---|---|---|---|---|---|
| | | Unit | 29 | 30 | 31 | 32 | 33 | 34 | 1 | 2 | 3 |
| Starting materials | 1,4-BAC | g | 100 | 100 | 100 | 100 | | | 100 | 100 | 100 |
| | | mol | 0.70 | 0.70 | 0.70 | 0.70 | | | 0.70 | 0.70 | 0.70 |
| | 1,3-BAC | g | | | | | 100 | 100 | | | |
| | | mol | | | | | 0.70 | 0.70 | | | |
| | Aldehyde | g | | 2.1 | 2.1 | 2.0 | 2.0 | 2.5 | | | |
| | | mol | | 0.017 | 0.017 | 0.017 | 0.017 | 0.017 | | | |
| | Ketone | g | 2.0 | | | | | | | | |
| | | mol | 0.017 | | | | | | | | |
| | Amine | g | | | | | | | | 2.0 | 4.0 |
| | | mol | | | | | | | | 0.017 | 0.033 |
| | NaNH$_2$ | g | 1.9 | | | | 2.0 | 2.0 | 1.9 | 0.7 | 4.0 |
| | | mol | 0.049 | | | | 0.050 | 0.050 | 0.049 | 0.018 | 0.100 |
| | NaH | g | | 2.1 | | | | | | | |
| | | mol | | 0.051 | | | | | | | |
| | Na | g | | | 4.0 | | | | | | |
| | | mol | | | 0.052 | | | | | | |
| | LiNH$_2$ | g | | | | 1.1 | | | | | |
| | | mol | | | | 0.050 | | | | | |
| Temperature | | °C. | | | | | 120 | | | | |
| Stirring rate | | rpm | | | | | 200 | | | | |
| Reaction time | | hours | | | | | 4 | | | | |
| Isomer composition (trans-isomer ratio %) changed with time | 0 hours | | 40 | — | — | 40 | 26 | 26 | 40 | 41 | 41 |
| | 1 hours | | | | | | | | | | |
| | 2 hours | | 75 | — | — | 63 | — | — | — | — | — |
| | 3 hours | | 79 | — | — | 79 | — | — | — | — | — |
| | 4 hours | | 81 | — | — | 82 | — | — | — | — | — |
| | | | 82 | 77 | 79 | 82 | 20 | 20 | 53 | 70 | 77 |
| Isomer composition (cis/trans) | | | 18/82 | 23/77 | 21/79 | 18/82 | 80/20 | 80/20 | 47/53 | 30/70 | 23/77 |
| Isomerization yield | | % | 81 | 93 | 95 | 88 | 94 | 93 | 100 | 91 | 89 |

1,4-BAC: 1,4-bis(aminomethyl)cyclohexane
1,3-BAC: 1,3-bis(aminomethyl)cyclohexane As mentioned above, according to the method for isomerizing a bis(aminomethyl)cyclohexane of the present invention, it was shown that an isomerization reaction of an industrially important compound, i.e., bis(aminomethyl)cyclohexane, can be simply and highly actively carried out without passing through a high-pressure reaction or complicated multi-stage process.

More specifically, in the isomerization reaction carried out by using 4-methylbenzyl amine in Comparative Example 2, it was found that the isomer composition (cis/trans) is low and the reaction efficiency is low. Also in Comparative Example 3 using larger amounts of 4-methylbenzyl amine and sodium amide than in Comparative Example 2, it was found that the reaction efficiency per raw material used therein is low and the cost for the isomerization reaction increases.

In Examples 15 to 17, it was demonstrated that an isomerization reaction is more accelerated by bubbling. In Examples 18 and 19, it was demonstrated that an isomerization reaction can be accelerated by use of a solvent having a lower boiling point than the isomerization reaction temperature. The isomerization reaction acceleration effect shown in Examples 15 to 19 is conceivably caused by removing by-products through bubbling or reflux; however, the cause is not limited to this.

The present application was made based on Japanese Patent Application No. 2013-191882 filed on Sep. 17, 2013 with Japan Patent Office; Japanese Patent Application No. 2014-056149 filed on Mar. 19, 2014 with the Japanese Patent Office; and Japanese Patent Application No. 2014-110871 filed on May 29, 2014 with the Japan Patent Office, the contents of which are incorporated herein by reference.

INDUSTRIAL APPLICABILITY

The bis(aminomethyl)cyclohexane obtained by the isomerization method of the present invention is used in a polyamide and a polyurethane and has industrial applicability as optical materials such as to plastic lenses, prisms, optical fibers, information recording substrates and filters using the polyamide and polyurethane.

The invention claimed is:
1. A method for isomerizing a bis(aminomethyl)cyclohexane, comprising:
an isomerization step of isomerizing the bis(aminomethyl)cyclohexane in the presence of:
an imine compound represented by formula (1) and
at least one compound selected from the group consisting of an alkali metal, an alkali metal-containing compound, an alkaline earth metal and an alkaline earth metal-containing compound:

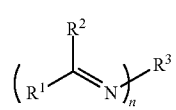

(1)

wherein R$^1$ and R$^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring); $R^3$ represents a hydrogen atom or an n-valent group selected from the group consisting of substituted or unsubstituted hydrocarbon groups; and n represents an integer of 1 to 10.

2. The method for isomerizing the bis(aminomethyl) cyclohexane according to claim 1, wherein the substituted or unsubstituted hydrocarbon group represented by each of $R^1$ and $R^2$ comprises a monovalent group selected from the group consisting of a substituted or unsubstituted aliphatic hydrocarbon group, a substituted or unsubstituted alicyclic hydrocarbon group and a substituted or unsubstituted aromatic hydrocarbon group; and the substituted or unsubstituted hydrocarbon group represented by $R^3$ comprises an n-valent group selected from the group consisting of a substituted or unsubstituted aliphatic hydrocarbon group, a substituted or unsubstituted alicyclic hydrocarbon group and a substituted or unsubstituted aromatic hydrocarbon group.

3. The method for isomerizing the bis(aminomethyl) cyclohexane according to claim 1, wherein the imine compound comprises a compound represented by the following general formula (2) and/or a compound represented by the following general formula (3):

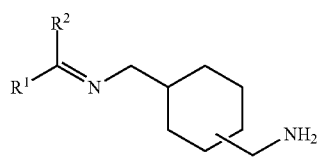

(2)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring);

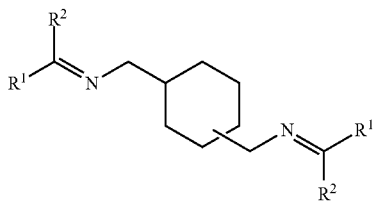

(3)

wherein $R^1$ and $R^2$ each independently represent a hydrogen atom or a monovalent group selected from the group consisting of a substituted or unsubstituted hydrocarbon group, a substituted or unsubstituted alkoxy group, a substituted or unsubstituted aryloxy group and an acyl group ($R^1$ and $R^2$ may mutually bind to form a ring).

4. The method for isomerizing the bis(aminomethyl) cyclohexane according to claim 2, wherein the aliphatic hydrocarbon group comprises a linear or branched and substituted or unsubstituted aliphatic hydrocarbon group.

5. The method for isomerizing the bis(aminomethyl) cyclohexane according to claim 2, wherein the alicyclic hydrocarbon group comprises an alicyclic hydrocarbon group having an amino group.

6. The method for isomerizing the bis(aminomethyl) cyclohexane according to claim 2, wherein the aromatic hydrocarbon group comprises a monovalent group selected from the group consisting of a substituted or unsubstituted benzyl group, a substituted or unsubstituted benzal group, a substituted or unsubstituted monovalent phenyl group and a substituted or unsubstituted monovalent naphthyl group.

7. The method for isomerizing the bis(aminomethyl) cyclohexane according to claim 1, wherein the imine compound is obtained by dehydration condensation between a primary amine and an aldehyde and/or a ketone.

8. The method for isomerizing the bis(aminomethyl) cyclohexane according to claim 1, wherein the imine compound is obtained by dehydration condensation between the bis(aminomethyl)cyclohexane and an aldehyde and/or a ketone.

9. The method for isomerizing the bis(aminomethyl) cyclohexane according to claim 7, wherein the aldehyde comprises at least one selected from the group consisting of an aliphatic aldehyde represented by the following general formula (6), an aromatic aldehyde represented by the following general formula (7) and an aromatic aldehyde represented by the following general formula (8):

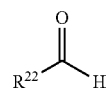

(6)

wherein $R^{22}$ represents a hydrogen atom or a monovalent substituent selected from the group consisting of a substituted or unsubstituted aliphatic hydrocarbon group and a substituted or unsubstituted alicyclic hydrocarbon group;

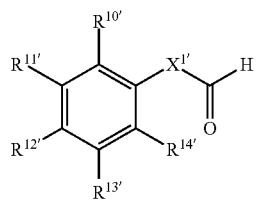

(7)

wherein $R^{10'}$, $R^{11'}$, $R^{12'}$, $R^{13'}$ and $R^{14'}$ each independently represent a hydrogen atom or at least one group selected from the group consisting of an alkyl group having 1 to 10 carbon atoms, an alkoxy group having 1 to 10 carbon atoms, a phenyl group and an amino group; and $X^{1'}$ represents a single bond or a divalent alkyl group having 1 to 10 carbon atoms;

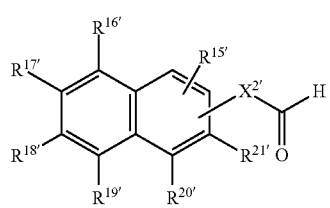

(8)

wherein $R^{15'}$, $R^{16'}$, $R^{17'}$, $R^{18'}$, $R^{19'}$, $R^{20'}$ and $R^{21'}$ each independently represent a hydrogen atom or at least one group selected from the group consisting of an alkyl group having 1 to 10 carbon atoms, an alkoxy group having 1 to 10 carbon atoms, a phenyl group and an amino group; and $X^{2'}$ represents a single bond or a divalent alkyl group having 1 to 10 carbon atoms.

10. The method for isomerizing the bis(aminomethyl) cyclohexane according to claim 8, wherein the aldehyde comprises:
  at least one aliphatic aldehyde selected from the group consisting of formaldehyde, acetaldehyde, isobutyraldehyde, n-decylaldehyde, methacrolein, cinnamaldehyde and glyoxal; and/or
  at least one aromatic aldehyde selected from the group consisting of benzaldehyde, 4-methylbenzaldehyde, 4-ethylbenzaldehyde, 4-isopropylbenzaldehyde, 4-isobutylbenzaldehyde, 2,4-dimethylbenzaldehyde, 3,4-dimethylbenzaldehyde, 2,4,5-trimethylbenzaldehyde, 2,4,6-trimethylbenzaldehyde and 4-biphenylaldehyde.

11. The method for isomerizing the bis(aminomethyl) cyclohexane according to claim 8, wherein the ketone comprises at least one selected from the group consisting of an aliphatic ketone, an aromatic ketone, an aliphatic aromatic ketone and a cyclic ketone.

12. The method for isomerizing the bis(aminomethyl) cyclohexane according to claim 8, wherein the ketone comprises at least one selected from the group consisting of methyl ethyl ketone and acetophenone.

13. The method for isomerizing the bis(aminomethyl) cyclohexane according to claim 1, wherein the alkali metal-containing compound comprises at least one selected from the group consisting of an alkali metal hydride and an alkali metal amide.

14. The method for isomerizing the bis(aminomethyl) cyclohexane according to claim 1, wherein the compound comprises at least one selected from the group consisting of metallic sodium, sodium amide and sodium hydride.

15. The method for isomerizing the bis(aminomethyl) cyclohexane according to claim 1, wherein the bis(aminomethyl)cyclohexane comprises 1,4-bis(aminomethyl)cyclohexane and/or 1,3-bis(aminomethyl)cyclohexane.

16. The method for isomerizing the bis(aminomethyl) cyclohexane according to claim 1, comprising, during and/or after the isomerization step, an isomer separation step of distilling a trans-isomer of 1,4-bis(aminomethyl)cyclohexane and/or a cis-isomer of 1,3-bis(aminomethyl)cyclohexane.

17. The method for isomerizing the bis(aminomethyl) cyclohexane according to claim 1, wherein an isomerization reaction temperature of the isomerization step is 100 to 140° C.

18. The method according to claim 1, wherein, in the isomerization step, bubbling is performed by an inert gas.

19. The method according to claim 1, wherein, in the isomerization step, a solvent having a boiling point equal to or lower than the isomerization reaction temperature is further used.

20. The method for isomerizing the bis(aminomethyl) cyclohexane according to claim 1, wherein 1,3-bis(aminomethyl)cyclohexane having a cis-isomer content of 80% or more or 1,4-bis(aminomethyl)cyclohexane having a trans-isomer content of 75% or more is obtained.

* * * * *